US011401563B2

(12) United States Patent
Dabrowska-Schlepp et al.

(10) Patent No.: US 11,401,563 B2
(45) Date of Patent: Aug. 2, 2022

(54) GLYCOSYLATED LYSOSOMAL PROTEINS, METHOD OF PRODUCTION AND USES

(71) Applicant: eleva GmbH, Freiburg (DE)

(72) Inventors: Paulina Dabrowska-Schlepp, Gundelfingen (DE); Fode Benjamin, Denzlingen (DE); Andreas Busch, Ebringen (DE); Holger Niederkrüger, Malterdingen (DE); Andreas Schaaf, Freiburg (DE)

(73) Assignee: eleva GmbH, Freiburg (DE)

( * ) Notice: Subject to any disclaimer, the term of this patent is extended or adjusted under 35 U.S.C. 154(b) by 276 days.

(21) Appl. No.: 15/542,998

(22) PCT Filed: Mar. 17, 2016

(86) PCT No.: PCT/EP2016/055830
§ 371 (c)(1),
(2) Date: Jul. 12, 2017

(87) PCT Pub. No.: WO2016/146760
PCT Pub. Date: Sep. 22, 2016

(65) Prior Publication Data
US 2018/0016648 A1      Jan. 18, 2018

(30) Foreign Application Priority Data
Mar. 17, 2015   (EP) .................. 15159443

(51) Int. Cl.
*C12N 9/24* (2006.01)
*C12N 9/40* (2006.01)
(Continued)

(52) U.S. Cl.
CPC ........ *C12Y 302/01021* (2013.01); *C12N 5/04* (2013.01); *C12N 9/10* (2013.01);
(Continued)

(58) Field of Classification Search
None
See application file for complete search history.

(56) References Cited

U.S. PATENT DOCUMENTS 6,083,725 A    7/2000  Selden et al.
6,887,696 B2   5/2005  Garger et al.
(Continued)

FOREIGN PATENT DOCUMENTS

EP     2 789 686 A1     10/2014
JP     2005-535291 A    11/2005
(Continued)

OTHER PUBLICATIONS

GenBank Accession No. M74715.1, published Nov. 22, 1995 (Year: 1995).*

(Continued)

*Primary Examiner* — Richard C Ekstrom
(74) *Attorney, Agent, or Firm* — Birch, Stewart, Kolasch & Birch, LLP

(57) ABSTRACT

The present invention relates to a lysosomal protein composition comprising a plurality of lysosomal proteins that are potentially diversely glycosylated according to a glycosylation pattern, wherein said glycosylation pattern has at least 45% paucimannosidic N-glycans; a method of manufacturing the lysosomal protein composition in a bryophyte plant or cell, and medical and non-medical uses of the lysosomal protein composition. E.g. the lysosomal protein can be a-Galactosidase for the treatment of Fabry Disease or β-Glucoceramidase for the treatment of Gaucher's Disease. The unique glycosylation results in improved therapeutic efficacy—surprisingly even without mannose-6-phosphate that is common for CHO cell produced lysosomal proteins.

Figure 1:

15 Claims, 12 Drawing Sheets
Specification includes a Sequence Listing.

(51) Int. Cl.
  C12N 15/82    (2006.01)
  C12N 5/04     (2006.01)
  C12N 9/10     (2006.01)
(52) U.S. Cl.
  CPC ......... *C12N 9/2402* (2013.01); *C12N 9/2465* (2013.01); *C12N 15/8257* (2013.01); *C12Y 302/01022* (2013.01); *C12Y 302/01045* (2013.01)

(56)         References Cited

U.S. PATENT DOCUMENTS

| | | | |
|---|---|---|---|
| 7,011,831 | B2 | 3/2006 | Calhoun et al. |
| 2006/0040353 | A1 | 2/2006 | Davidson et al. |
| 2006/0253928 | A1 | 11/2006 | Bakker et al. |
| 2008/0141387 | A1* | 6/2008 | Reski ................ C12N 15/8257 800/278 |
| 2008/0201804 | A1 | 8/2008 | Gorr et al. |
| 2009/0291078 | A1 | 11/2009 | Schuster et al. |
| 2011/0045533 | A1 | 2/2011 | Cadoret et al. |
| 2015/0147811 | A1 | 5/2015 | Thomas et al. |
| 2018/0016648 | A1* | 1/2018 | Dabrowska-Schlepp .................... C12Y 302/01021 |

FOREIGN PATENT DOCUMENTS

| | | |
|---|---|---|
| JP | 2006-511234 A | 4/2006 |
| JP | 2009-201011 A | 1/2009 |
| JP | 2009-542750 A | 12/2009 |
| JP | 2010-525806 A | 7/2010 |
| JP | 2011-512128 A | 4/2011 |
| JP | 2014-139204 A | 7/2014 |
| JP | 2014-221077 A | 11/2014 |
| WO | WO 02/08404 A2 | 1/2002 |
| WO | WO 03/073839 A2 | 9/2003 |
| WO | WO 03/078637 A2 | 9/2003 |
| WO | WO 2004/057002 A2 | 7/2004 |
| WO | WO 2008/132743 A2 | 11/2008 |
| WO | WO 2010/075010 A2 | 7/2010 |
| WO | WO 2011/107990 A1 | 9/2011 |
| WO | WO 2012/098537 A1 | 7/2012 |
| WO | WO 2014/013045 A1 | 1/2014 |

OTHER PUBLICATIONS

GenBank Accession No. AAA35873.1, published Apr. 27, 1993 (Year: 1993).*
International Search Report (PCT/ISA/210) issued in PCT/EP2016/055830, dated May 19, 2016.
Search Report issued in European Patent Application No. 15159443.9 dated Jun. 1, 2015.
Weise et al., "High-level expression of secreted complex glycosylated recombinant human erythropoietin in the Physcomitrella Δ-fuc-t Δ-xyl-t mutant", Plant Biotechnology Journal, vol. 5, 2007, pp. 389-401.
Written Opinion (PCT/ISA/237) issued in PCT/EP2016/055830, dated May 19, 2016.
He et al., "Production of α-$_L$-iduronidase in Maize for the Potential Treatment of a Human Lysosomal Storage Disease," Nature Communications, vol. 3, 2012, p. 1062 (9 pages total).
Office Action dated Oct. 16, 2019 in European Patent Application No. 16 714 275.1.
Schaaf, et al., "Use of endogenous signal sequences for transient production and efficient secretion by moss (*Physcomitrella patens*) cells" BMC Biotechnology, 2005, vol. 5, No. 30, pp. 1-11.
Koprivova et al., "N-Glycosylation in the Moss *Physcomitrella patens* is Organized Similarly to that in Higher Plants," Plant Biology, vol. 5, 2003, pp. 582-591.
Koprivova et al., "Targeted knockouts of Physcomitrella lacking plant-specific immunogenic N-glycans," Plant Biotechnology Journal, vol. 2, 2004, pp. 517-523.

Partial translation of the Japanese Office Action for Japanese Application No. 2017-548840, dated Dec. 17, 2019.
Vietor at al., "Protein N-glycosylation is similar in the moss *Physcomitrella patens* and in higher plants," Planta, vol. 218, 2003, pp. 269-275 (8 pages total).
Chinese Office Action and Search Report dated Aug. 18, 2020 for Application No. 201680016207.5 along with an English translation.
Baur et al., "A Fast and Flexible PEG-mediated Transient Expression System in Plants for High Level Expression of Secreted Recombinant Proteins," Journal of Biotechnology, vol. 119, 2005, pp. 332-342.
Bosch et al., "N-Glycosylation of Plant-produced Recombinant Proteins," Current Pharmaceutical Design, vol. 19, No. 31, 2013, pp. 5503-5512.
Castilho et al., "Glyco-engineering in Plants to Produce Human-like N-glycan Structures," Biotechnology Journal, vol. 7, Sep. 2012, pp. 1088-1098 (Total 13 pages).
Chiba et al., "Production in Yeast of α-galactosidaseA, a Lysosomal Enzyme Applicable to Enzyme Replacement Therapy for Fabry Disease," Glycobiology, vol. 12, No. 12, 2002, pp. 821-828.
Cox et al., "Glycan Optimization of a Human Monoclonal Antibody in the Aquatic Plant Lemna minor," Nature Biotechnology Advanced Online Publication, vol. 24, No. 12, Published online Nov. 26, 2006, pp. 1591-1597.
De Marchis et al., "Human α-mannosidase Produced in Transgenic Tobacco Plants is Processed in Human α-mannosidosis Cell Lines," Plant Biotechnology Journal, vol. 9, 2011, pp. 1061-1073.
Du et al., "Wolman Disease/cholesteryl Ester Storage Disease: Efficacy of Plant-produced Human Lysosomal Acid Lipase in Mice," Journal of Lipid Research, vol. 49, 2008 (Published, JLR Papers in Press, Apr. 15, 2008), pp. 1646-1657.
Durant et al., "Sex Differences of Urinary and Kidney Globotriaosylceramide and Lyso-globotriaosylceramide in Fabry Mice," Journal of Lipid Research, vol. 52, 2011 (Published, JLR Papers in Press, Jul. 11, 2011), pp. 1742-1746.
He et al., "Production of α-L-iduronidase in Maize for the Potential Treatment of a Human Lysosomal Storage Disease," Nature Communications, vol. 3, 2012, p. 1062 (9 pages total).
Hohe et al., "Control of Growth and Differentiation of Bioreactor Cultures of Physcomitrella by Environmental Parameters," Plant Cell, Tissue and Organ Culture, vol. 81, 2005, pp. 307-311.
Kizhner et al., "Characterization of a Chemically Modified Plant Cell Culture Expressed Human α-Galactosidase-A Enzyme for Treatment of Fabry Disease," Mol. Genet. Metab., vol. 114, No. 2, 2014, pp. 259-267.
Liebminger et al., "β-N-Acetylhexosaminidases HEXO1 and HEXO3Are Responsible for the Formation of Paucimannosidic N-Glycans in Arabidopsis thaliana," The Journal of Biological Chemistry, vol. 286, No. 12, Mar. 25, 2011 (Published online Jan. 20, 2011), pp. 10793-10802 (11 pages).
Rayon et al., "The Protein N-glycosylation in Plants," Journal of Experimental Botany, vol. 49, No. 326, Sep. 1998, pp. 1463-1472.
Reski, "Development, Genetics and Molecular Biology of Mosses," Bot. Acta, vol. 111, 1998, pp. 1-15.
Reutter et al., "Production of a Heterologous Protein in Bioreactor Cultures of Fully Differentiated Moss Plants," Plant Tissue Culture and Biotechnology, vol. 2, No. 3, Sep. 1996, pp. 142-147.
Rudolph et al., "Studies on Secondary Metabolism of Sphagnum Cultivated in Bioreactors," Crypt. Bot., vol. 3, 1992, pp. 67-73 (Total 4 pages).
Sands et al., "Biodistribution, Kinetics, and Efficacy of Highly Phosphorylated and Non-phosphorylated β-Glucuronidase in the Murine . . . ," The Journal of Biological Chemistry, vol. 276, No. 46, Nov. 16, 2001 (Published, JBC Papers in Press, Sep. 18, 2001), pp. 43160-43165 (Total 7 pages).
Shaaltiel et al., "Production of Glucocerebrosidase with Terminal Mannose Glycans for Enzyme Replacement Therapy of Gaucher's Disease Using a Plant Cell System," Plant Biotechnology Journal, vol. 5, 2007, pp. 579-590.
Shen et al., "Globotriaosylceramide Induces Oxidative Stress and Up-regulates Cell Adhesion Molecule Expression in Fabry Disease Endothelial Cells," Molecular Genetics and Metabolism, vol. 95, 2008 (Available online Aug. 15, 2008), pp. 163-168.

(56) References Cited

OTHER PUBLICATIONS

Shen et al., "Isofagomine Increases Lysosomal Delivery of Exogenous Glucocerebrosidase," Biochemical and Biophysical Research Communications, vol. 369, 2008 (Available online Mar. 6, 2008), pp. 1071-1075.

Sly et al., "Enzyme Therapy in Mannose Receptor-null Mucopolysaccharidosis VII Mice Defines Roles for the Mannose 6-phosphate and Mannose Receptors," PNAS, vol. 103, No. 41, Oct. 10, 2006, pp. 15172-15177.

Stemmer et al., "Marker-free Transformation of Physcomitrella patens," Moss 2004, The 7th Annual Moss International Conference, Freiburg, Germany, 2004, 1 page.

Strepp et al., "Plant Nuclear Gene Knockout Reveals a Role in Plastid Division for the Homolog of the Bacterial Cell Division Protein FtsZ, an Ancestral Tubulin," Proc. Natl. Acad. Sci. USA, vol. 95, Apr. 1998, pp. 4368-4373.

Tsukimura et al., "Efficient Uptake of Recombinant α-Galactosidase A Produced with a Gene-Manipulated Yeast by Fabry Mice Kidneys," Mol. Med., vol. 18, 2012 (Epub ahead of print Oct. 21, 2011), pp. 76-82.

Weise et al., "Use of Physcomitrella patens Actin 5' Regions for High Transgene Expression: Importance of 5' Introns," Appl Microbiol Biotechnol, vol. 70, 2005, pp. 337-345 (9 pages total).

* cited by examiner

Fig. 3
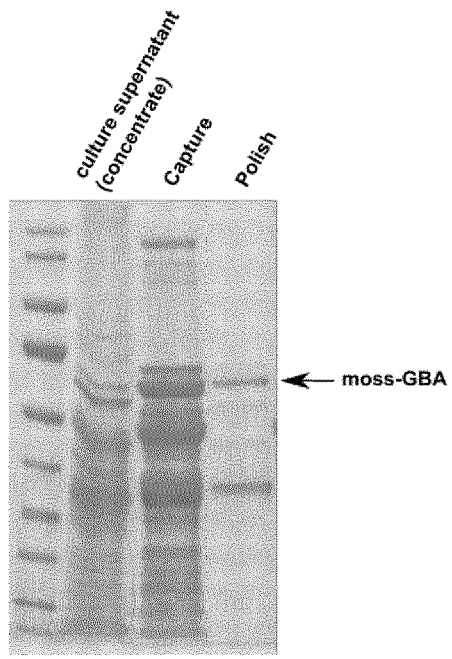
Fig. 4    A                                    B
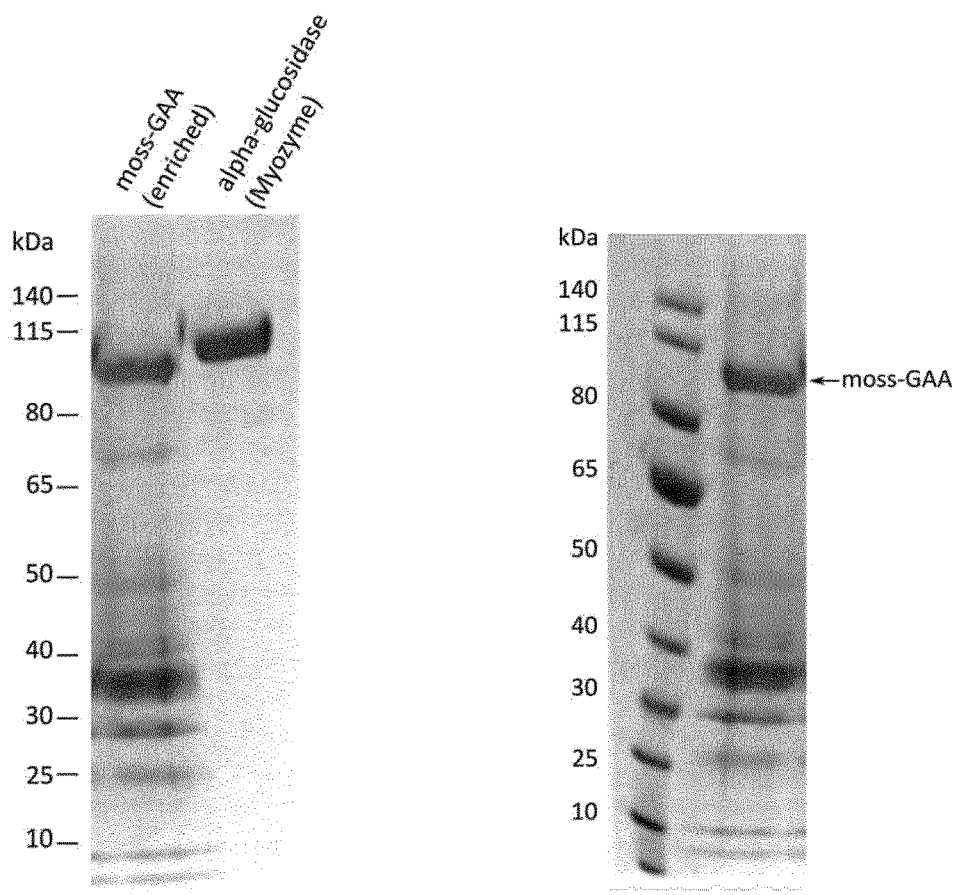

GLYCOSYLATED LYSOSOMAL PROTEINS, METHOD OF PRODUCTION AND USES

The present invention relates to the field of recombinant protein expression in plants for obtaining a modified glycosylation as compared to mammalian expression systems.

BACKGROUND

Lysosomal storage diseases (LSDs) are a group of life-threatening inherited disorders; most of them are caused by deficiency of a single lysosomal enzyme or protein, which leads to abnormal accumulation of substrate in cells. Currently, enzyme replacement therapy (ERT) is the only available specific treatment for several LSDs. In these diseases, lysosomal storage can be cleared in many target tissues by intravenous infusion of the missing enzyme. Traditionally, recombinant enzymes used in ERT are produced in cultured mammalian cells. E.g. U.S. Pat. No. 6,083,725 describes an α-galactosidase from human cells. Recently, as an alternative approach, plant-based expression systems have been utilized to produce lysosomal enzymes for therapeutic use (Shaaltiel et al. (2007) Plant Biotechnol J 5:579-590; Du et al. (2008) J Lipid Res 49:1646-1657; De Marchis et al. (2011) Plant Biotechnol J 9:1061-1073; He et al. (2012) Nat Commun 3:1062). Relative to mammalian cell-based systems, plant-based systems have several advantages including lower production costs, eliminated risk of contamination by mammalian pathogens and, in the case of moss, a relatively easier manipulation of the N-glycosylation pathway. However, a major concern of plant cell-produced enzymes for ERT is their N-glycan structures that differ from mammalian cell-produced enzymes. Particularly, lysosomal enzymes expressed in plant cells typically do not acquire mannose 6-phosphate (M6P) modification on terminal mannose restudies without further artificial phosphorylation. Sugar chains exert a pivotal role in ERT. Intravenously administered lysosomal enzymes are taken up by tissues through cell surface receptors that recognize carbohydrate structure of the enzymes. M6P receptor (M6PR) and mannose receptor (MR) represent two major contributors for this uptake system.

Most lysosomal enzymes carry M6P residues. It is generally believed that in the ERT for most LSDs the M6PR-mediated endocytic pathway is crucial for sufficient enzyme delivery (Sly et al. (2006) Proc Natl Acad Sci USA 103: 15172-15177; Sands et al. (2001) J Biol Chem 276:43160-43165). MR—on the contrary—is present on macrophages and is believed to facilitate only therapeutic effect of ERT aiming at enzyme substitution in these cells.

WO 02/08404 and WO 2012/098537 describe the production of various lysosomal enzymes in tobacco.

WO 03/073839 describes the production of lysosomal enzymes in plant seeds, especially in seeds of tobacco plants.

U.S. Pat. No. 7,011,831 describes the production of lysosomal enzymes with complex N-glycan glycosylation in insect cells.

WO 2008/132743 describes the production of high mannose glycosylated lysosomal enzymes in tobacco using an expression construct with ER signal peptide and a vacuolar targeting signal.

EP 2 789 686 A1 describes the modification of plant glycosylation pathways to produce mammalian-type phosphorylated glycans.

US 2006/040353 describes transferring beta-galactose onto N-linked glycans. Glycoproteins with mannose-6-phosphate are suggested for treatment of lysosomal diseases.

Chiba et al. produced human α-gal A from yeast S. cerevisiae (Chiba et al. (2002) Glycobiology 12:821-828). In that case, M6P is covered by terminal mannose, and the removal of mannose residues by bacterial α-mannosidase led to improved M6PR-dependent uptake of the enzyme in cultured fibroblasts. Recently, α-gal A was expressed in another gene-manipulated yeast strain, which overexpresses MNN4, a positive regulator of mannosylphosphate transferase (Tsukimura et al. (2012) Mol Med 18:76-82). Phosphorylated N-glycan content in this α-gal A preparation was higher than that in agalsidase alfa (28.7% vs. 15.3%). Repeated injection of this enzyme into Fabry mice resulted in similar decrease of cardiac and renal $Gb_3$ to that in agalsidase alfa-injected mice. Most recently, Kizhner et al. reported the purification and characterization of human α-gal A produced from Tobacco cell culture (Kizhner et al. (2015) Mol Genet Metab 114(2): 259-267). As other plant-made lysosomal enzymes, this aGal is non-phosphorylated. However, this protein is chemically cross-linked and PEGylated. These modifications are associated with significant changes in protein characteristics including increased in vitro stability and dramatically prolonged circulation half-life (~10 hr) when compared with agalsidase alfa or beta. The uptake mechanism of this enzyme remains to be elucidated. However, remarkably slow plasma clearance suggests that the uptake is not via M6PR- or MR-mediated endocytosis.

U.S. Pat. No. 6,887,696 describes a method for the expression of two lysosomal proteins, i.e. alpha-glucocerebrosidase and alpha-galactosidase, in tobacco plants, a higher plant. The tobacco produced lysosomal proteins had a diverse glycosylation pattern, having high amounts of complex N-glycans, especially GnMXF, MGnXF, GnGnXF, GnMx and MGnX.

The goal of the invention is to provide an alternative source for the production of lysosomal proteins, which are active as therapeutics for the treatment of lysosomal storage diseases requiring a suitable glycosylation.

SUMMARY OF THE INVENTION

This goal of the present invention is solved by the present invention, which is based on the surprising findings that i) paucimannosidic glycosylations on lysosomal proteins bestow suitability for treatment options and ii) that such paucimannosidic glycosylations can be easily obtained in bryophyte expression systems.

The present invention provides a method of manufacturing a lysosomal protein composition comprising expressing a transgene encoding a lysosomal protein in a bryophyte plant or cell, wherein said lysosomal protein is expressed with a N-terminal secretory signal, wherein said secretory signal is optionally removed during intracellular processing, especially wherein the lysosomal protein lacks a C-terminal vacuolar signal with the sequence VDTM (SEQ ID NO: 1), and said method further comprises obtaining an expressed lysosomal protein from said plant or cell. The invention further provides a lysosomal protein composition obtainable by the inventive method.

The invention further provides a lysosomal protein composition comprising a plurality of lysosomal proteins that are potentially diversely glycosylated according to a glycosylation pattern, wherein said glycosylation pattern has at least 45% paucimannosidic N-glycans (molar %). Such a protein composition can be obtained by the inventive method.

Also provided a method of processing a lysosomal protein comprising a complex N-glycan, said method comprising providing the lysosomal protein in a sample and contacting the sample with a bryophyte HEXO, preferably HEXO3, enzyme, whereby the bryophyte HEXO enzyme cleaves terminal GlcNAc residues from the lysosomal protein thereby producing a paucimannosidic N-glycan. The HEXO enzyme may be in a cell, especially a plant cell. The lysosomal proteins can be provided as a medicament or in a pharmaceutical composition.

The invention also provides a bryophyte cell or plant suitable for performing the inventive method comprising said transgene encoding a lysosomal protein.

The invention also relates to a method of treatment of a lysosomal storage disease comprising administering a lysosomal protein composition according to the invention to a patient in need of treatment.

All these aspects are interrelated, equally form part of the entire invention presented herein and preferred embodiments of the invention in any combination may relate to any one of these aspects, e.g. plants or cells transformed by a given construct or method can be provided or used in the production of any lysosomal protein to be glycosylated according to the invention. The following detailed description on any embodiment or preferred feature relates to all aspects equally. E.g. a product feature of the lysosomal protein means that the method is selected to produce this lysosomal protein with its product feature. A description of particular method steps is equally descriptive of the protein modified by this method step. The inventive cell is transformed to facilitate any inventive method of manufacture in the cell. All lysosomal proteins can be used in the inventive methods of (therapeutically or non-therapeutically) using the lysosomal protein. The present invention is further defined in the claims.

DETAILED DESCRIPTION OF THE INVENTION

Lysosomal storage diseases (LSD) are a group of approximately 50 rare inherited metabolic disorders that result from defects in lysosomal function. Lysosomes are responsible for digesting various molecules involving several critical enzymes. If one of these enzymes is defective, because of a mutation, the large molecules accumulate within the cell, eventually killing it. Lysosomal storage disorders are caused by lysosomal dysfunction usually as a consequence of deficiency of a single enzyme required for the metabolism of lipids, glycoproteins or mucopolysaccharides.

Treatment of lysosomal storage diseases is mostly symptomatic, with enzyme replacement therapy being the most common. ERT requires administration of active lysosomal proteins into the cells via an uptake route.

Traditionally, recombinant enzymes used in ERT are produced in cultured mammalian cells. Recently, as an alternative approach, plant-based expression systems have been utilized to produce lysosomal enzymes for therapeutic use. Relative to mammalian cell-based systems, plant-based systems have several advantages including lower production costs, eliminated risk of contamination by mammalian pathogens and, in the case of moss, a relatively easier manipulation of the N-glycosylation pathway. However, a major concern when considering using plant cell-produced enzymes for ERT is their N-glycan structures that differ from mammalian cell-produced enzymes. Particularly, lysosomal enzymes expressed in plant cells typically do not acquire mannose 6-phosphate (M6P) modification on terminal mannose residues.

The present invention provides a new method of producing transgenic lysosomal proteins in plant cells, especially in bryophyte cells, which surprisingly led to the formation of glycoproteins with a high degree of paucimannosidic glycosylation, i.e. a glycosylation terminating with few, e.g. 2 mannose residues, in a branched -Man<(Man)$_2$ structure. These structures have proven to be highly effective for the uptake, especially in cells affected by lysosomal storage disease. This altered glycosylation is unnatural for the lysosomal proteins, yet surprisingly the altered proteins are still very effective therapeutic proteins.

The lysosomal protein used in the inventive method is a transgene, e.g. of mammalian origin, for use in ERT in that mammal of origin. These transgenic lysosomal proteins produced in bryophytes can be used as therapeutic proteins for the treatment of lysosomal storage diseases. As such, the lysosomal proteins are active enzymes when administered, in particular active in conditions occurring in a lysosome, such as a pH of about 5. Of course inactive storage forms, e.g. when lyophilized, are possible. The inventive paucimannosidic glycosylation does not substantially interfere with enzymatic activity but mediates uptake and stability of the lysosomal proteins. Surprisingly, the inventive N-glycans on the lysosomal proteins lead to high efficacy allowing a therapeutic use thereof especially in the treatment of lysosomal storage diseases.

The present invention can rely on known methods for introducing transgenes into bryophytes. Suitable transformation systems have been developed for the biotechnological exploitation of bryophytes for the production of heterologous proteins. For example, successful transformations have been carried out by direct DNA transfer into protonema tissue using particle guns. PEG-mediated DNA transfer into moss protoplasts has also been successfully achieved. The PEG-mediated transformation method has been described many times for *Physcomitrella patens* and leads both to transient and to stable transformants (K. Reutter and R. Reski, Pl. Tissue culture and Biotech., 2, 142-147 (1996)). Moreover, marker-free transformation can be achieved by PEG-mediated transformation method with bryophytes as well (Stemmer C, Koch A and Gorr G (2004), Moss 2004, The 7th Annual Moss International Conference, Freiburg, Germany) and can be used for subsequent introduction of multiple nucleotide sequences.

Detailed information on the culturing of bryophytes which are suitable for use in the invention, such as *Leptobryum pyriforme* and *Sphagnum magellanicum* in bioreactors, is known in the prior art (E. Wilbert, "Biotechnological studies concerning the mass culture of mosses with particular consideration of the arachidonic acid metabolism", Ph.D. thesis, University of Mainz (1991); H. Rudolph and S. Rasmussen, Crypt. Bot., 3, 67-73 (1992)). Especially preferred for the purposes of the present invention is the use of *Physcomitrella patens*, since molecular biology techniques are practiced on this organism (R. Reski Bot. Acta, 111, pp. 1-15 (1998)). For cultivation of bryophytes media with (Baur et al. (2005) Plant Biotechnol J 3, 331-340) or without supplements like trace elements can be used (Weise et al. (2006) Appl. Microbiol. Biotechnol., 70, 337-345).

The inventive method of manufacturing a lysosomal protein composition preferably comprises expressing a transgene encoding a lysosomal protein in a bryophyte plant or cell, wherein said lysosomal protein is expressed with a N-terminal secretory signal and the lysosomal protein lacks a C-terminal vacuolar signal with the sequence VDTM (SEQ ID NO: 1). This would avoid vacuolar targeting, which would lead to storage of the lysosomal protein in the vacuole (contrary to excretion) and potentially to different glycol-processing in the vacuole, wherein still paucimannosidic glycoforms are still possible to some extent. In the golgi, without vacuole targeting, based on bryophyte specific recombinant protein interaction, a different glycosylation pathway surprisingly led to high amounts of paucimannosidic glycosylation independent of vacuole processing. This is very surprising since in tobacco the secretory, non-vacuole pathway led to the formation of predominantly complex N-glycans instead of paucimannosidic glycosylation (U.S. Pat. No. 6,887,696). Apparently, bryophytes have a unique recognition of lysosomal proteins leading to this modification.

SEQ ID NO: 1 is a C-terminal plant vacuolar targeting signal leading to efficient vacuole targeting. In some embodiments, other vacuole targeting signals may be present, especially non-plant signals, leading to less efficient vacuole targeting and some expression down the secretory pathway avoiding the vacuole. However, in most preferred embodiments, no vacuole targeting signal is present during expression or even in the final obtained product. Vacuolar signals may also be removed in artificially after obtaining the protein from the cells.

Paucimannosidic N-glycans are based on trimming of complex N-glycans. In the golgi, the terminal GlcNAc is removed from complex glycans leaving a terminal mannose, in case of the bryophyte system, this is very efficient leaving terminal mannose on both branches of the (formerly complex) N-glycan.

According to the invention, a secretory signal sequence is used, usually on the N-terminus of the amino acid sequence. The N-terminal secretory signal is also referred to as a transit peptide or ER signal sequence. It is part of the encoded and expressed amino acid sequence. The secretory signal leads to an expression directly into the ER of a cell, setting the pathways for secretion (or to vacuolar designation if a vascular signal is present. The secretory signal is usually removed intrinsically from the protein amino acid sequence during expression. This is a natural process in a plant cell. To allow proper localization of the expression product of the transgenes, the genes for the lysosomal proteins can be modified to allow for localization in the plant cell. Preferably hybrid nucleic acid sequences are used in the constructs for the transformation of the plants or plant cells. Localization-relevant domains of the e.g. mammalian enzymes are replaced by plant sequences to achieve correct localization and cellular transit such as in the ER and/or golgi in planta. An example of a plant secretory signal is SEQ ID NO: 5, but any other plant secretory signal may be used. It may be an endogenous sequence to the used bryophyte species or it may be a foreign plant sequence, but preferably still a bryophyte sequence.

The inventive method includes expression of the lysosomal protein without a plant (bryophyte) vacuolar signal, which has the sequence VDTM (SEQ ID NO: 1). This leads to an expression pathway from the ER to the golgi and eventually to secretion, avoiding the end-localization in a vacuole. In bryophytes, the secretion can be directly into the culturing medium. In other plants it may be to an apoplastic compartment of the plant cell. Surprisingly, even without vacuole placement, a high degree of paucomannosidic glycosylation could be achieved by the inventive method.

As a final step, the expressed lysosomal protein from said plant or cell is then obtained. To this end, the lysosomal protein may be collected from an extraction process from the cells, which may be disruptive or non-disruptive. Preferably the expressed lysosomal protein is obtained from secreted matter of the plant or cell, e.g. from the culture medium, preferably without disrupting the producing cells or plant. The obtained lysosomal protein may then be purified, e.g. to a concentration of at least 80% (m/v), preferably at least 90% (m/v), especially preferred at least 95% (m/v), or at least 98% (m/v) or at least 99% (m/v).

Preferably the bryophyte plant or cell is a moss, preferably *P. patens*, plant or cell. The bryophyte may be any bryophyte but is preferably selected from moss, liverwort or hornwort, especially preferred of the class bryopsida or of the genera *Physcomitrella, Funaria, Sphagnum, Ceratodon, Marchantia* and *Sphaerocarpos*. *Physcomitrella patens* is a particularly preferred system as it has a high rate of homologous recombination.

Subject matter of the invention are plants and plant cells. "Plant cell" as used herein may refer to an isolated cell, a singularized cell, but also a cell in or of a plant tissue, preferably a tissue selected from callus, protonema, phloem, xylem, mesophyll, trunk, leaves, thallus, chloronema, caulonema, rhizoid or gametophore, or a cell in a plant organism. The cell may be a protoplast cell. In preferred embodiments, isolated plant cells or even plant tissues are transformed according to the invention and then grown into plants or plant tissues, or remain plant cell cultures, such as a suspension culture, e.g. a bioreactor (Hobe & Reski, Plant Cell, Tissue and Organ Culture 81, 2005: 307-311).

Preferably the lysosomal protein further lacks a C-terminal ER retention signal with the sequence KDEL (SEQ ID NO: 2). ER retention signals lead to a retention in the ER or golgi system. This can have a profound impact on the glycosylation pattern observed in the expressed protein since glycosylation is a competitive process with several glycosylating enzymes vying for the substrate proteins to be modified. Although one could have expected that paucimannosidic trimming would benefit from ER retention, surprisingly the inventive lysosomal proteins were expressed with high amounts of paucimannosidic N-glycans without this (or any) ER retention signal.

SEQ ID NO: 2 is a C-terminal ER retention signal leading to efficient ER or golgi retention. Also, preferred the C-terminal di-lysine motif (KXKX), also responsible for ER retention to some extent, is also missing. In some embodiments, other ER retention signals may be present, especially non-plant signals, leading to less efficient ER/golgi retention and faster processing from compartment to compartment towards secretion. However, in most preferred embodiments, no ER retention signal is present during expression or even in the final obtained product. ER retention signals may also be removed artificially after obtaining the protein from the cells.

Especially preferred for any embodiment of the present invention, the lysosomal protein lacks a plant C-terminal ER retention signal sequence and a plant C-terminal vacuolar signal sequence, especially preferred, it lacks any C-terminal ER retention signal sequence and any C-terminal vacuolar signal sequence. Plant signals are from plant origin and found in plants, especially bryophytes. They are functional in bryophytes. As explained above, ER retention is not necessary and even vacuolar processing is not required for the high paucimannosidic glycosylation in the inventive bryophyte expression systems.

Preferably the lysosomal protein comprises an expressed amino acid sequence that terminates on the C-terminus with the amino acids of a native lysosomal protein or a truncation thereof This means that no additions to the proteins sequence are present. Truncations are possible, even if not preferred. Of course the truncations do not substantially affect activity of the inventive lysosomal protein, that is still a requirement as explained above. Enzymatic activity may be reduced by e.g. up to 20% when compared to the native lysosomal protein in lysosomal conditions in a mammalian, especially human, cell, such as at a pH of 5. The truncations may be a deletion of at most 50, preferably at most 40, at most 30, at most 20, at most 10, at most 5 or one, or any range in between these values (e.g. 1 to 10 etc.) C-terminal amino acids of the native lysosomal protein. Truncated alpha-galactosidases are known to be active with such truncations as e.g. described in U.S. Pat. No. 6,887,696 B2 (incorporated herein by reference).

Preferably the bryophyte plant or cell does or does not comprise a HEXO3 transgene. HEXO3 is an enzyme that is found naturally in plants. It may be supplied (or not) as a transgene to even further increase HEXO3 activity. Introductions of transgenes may be facilitated by the same methods as the lysosomal protein transgene is incorporated into the plant or cell, e.g. by genomic recombinant hybridization or plasmid introduction. HEXO3 is said to be responsible for some pauimannosidic glycosylation in the apoplast lining plasma membrane of plants (Liebminger et al., J Biol Chem 2011, 286: 10793-10802; Bosch et al., Curr Pharm Des. 2013; 19(31):5503-12), however the HEXO activity found by Liebminger in *Arabidopsis thaliana* cannot explain the high paucimannosidic glycosylation found in bryophytes. Related enzyme HEXO1 is responsible for some vacuolar paucimannosidic glycosylation and HEXO2 seems to have little activity in *Arabidopsis*. There can be higher activity or better accessibility in bryophytes.

Apparently bryophyte HEXO is particularly highly active on lysosomal proteins. Therefore the present invention provides an in vitro method of processing a lysosomal protein comprising a complex N-glycan, said method comprising providing the lysosomal protein in a sample and contacting the sample with a bryophyte HEXO, preferably HEXO3, enzyme, whereby the bryophyte HEXO enzyme cleaves terminal GlcNAc residues from the lysosomal protein thereby producing a paucimannosidic N-glycan. In essence, the native lysosomal protein glycosylation pathway found in bryophytes can be also performed outside a bryophyte cell, especially in vitro with isolated HEXO enzymes, or in another cell, preferably plant cell by substituting that plant with an active HEXO enzyme from a bryophyte, especially a moss such as *P. patens*. This plant may be a non-bryophyte, e.g. a higher plant, or a bryophyte to increase HEXO, preferably HEXO3, gene load as detailed above.

Preferably the bryophyte plant or cell has suppressed or eliminated alpha1,3-fucosyltransferase and/or beta1,2-xylosyltransferase. Such plant enzymes can be reduced in activity or concentration, at least in the site of their natural activity such as the golgi. Enzymes that are preferably removed are alpha-1,3-fucosyltransferase and/or beta-1,2-xylosyltransferase as described in WO 2004/057002. Thus according to a preferred embodiment, said plant cell further has a reduced activity, preferably a complete loss of function, of alpha-1,3-fucosyltransferase and/or of beta-1,2-xylosyltransferase, in particular by knock-out, especially preferred by interrupting the alpha-1,3-fucosyltransferase and/or beta-1,2-xylosyltransferase encoding gene of said plant, preferably by a gene of any one of the recombinantly expressed proteins. This measure prevents formation of plant-type glycosylations that may be immunogenic in a mammal such as a human.

Also provided is a bryophyte cell or plant suitable for performing this method. The cell or plant comprises a transgene encoding a lysosomal protein as described for the method paratively and optionally any further modification or transgene as described above.

The present invention further provides a lysosomal protein composition obtainable by any method of manufacturing described herein. The lysosomal protein may have any characteristics as effected by a method or preferred variant or embodiment as described above. The lysosomal protein is usually obtained in a plurality of such lysosomal proteins, with the inventive lysosomal glycosylation pattern observed in bryophytes for (transgenic) lysosomal proteins.

Especially, the invention provides a lysosomal protein composition comprising a plurality of lysosomal proteins that are potentially diversely glycosylated according to a glycosylation pattern, wherein said glycosylation pattern has at least 45%, preferably at least 50%, at least 55%, at least 60%, at least 65%, or at least 70%, paucimannosidic N-glycans.

All percentage values given herein are molar percentages, except where indicated otherwise.

A plurality relates to preparation of the inventive proteins comprising, i.e. not individualized proteins but a macroscopic preparation of such proteins as obtained from the cells or plants, which comprises more than one lysosomal protein when expressed. The preparation may have at least 1000 protein molecules, especially preferred at least 100000 molecules or at least 1 million molecules.

Preferably the lysosomal protein of the composition or produced or used by or in the inventive methods is any one selected from α-Galactosidase, preferably α-Galactosidase A (GLA); β-Glucoceramidase, β-glucosidase (glucocerebrosidase); α-Mannosidase; Aspartylglucosaminidase; β-Mannosidase; Acid Ceremidase; α-Fucosidase; β-Galactosidase, β-Hexosaminidase activator protein; Galactocerebrosidase, Galactoceramidase; lysosomal acid lipase (LAL); α-Iduronidase; Iduronate-2-sulfatase; Glucosamine-N-sulfatase, Heparansulfatsulfamidase (SGSH); α-N-acetyl-glucosaminidase (NAGLU); (Heparan)α-glucosaminide-N-acetyltransferase; N-Acetygalactosamine-6-sulfatase; β-Galactosidase; N-Acetygalactosamine-4-sulfatase; β-Glucoronidase; Neuraminidase; Sphingomyelinase, Sphingomyelin phosphodiesterase; Acid alpha-1,4-glucosidase; β-Hexosaminidase, or its α subunit; Alpha-N-acetylgalactosaminidase (NAGA), α-Galactosaminidase; β-Hexosaminidase A; Galactose-6-sulfate sulfatase; Hyaluronidase. Especially preferred in all embodiments of the invention is α-Galactosidase. A preferred α-Galactosidase is human α-Galactosidase, e.g. of SEQ ID NO: 3, which can be expressed from the nucleic acid sequence of SEQ ID NO: 4, or a truncated α-Galactosidase therefrom. Also preferred is glucocerebrosidase, e.g. human glucocerebrosidase e.g. of SEQ ID NO: 6, which can be expressed from the nucleic acid sequence of SEQ ID NO: 7. Also preferred is alpha-glucosidae, e.g. human alpha-glucosidae e.g. of SEQ ID NO: 8, which can be expressed from the nucleic acid sequence of SEQ ID NO: 9. In other embodiments, glucocerebrosidase and alpha-glucosidase are excluded from the group of lysosomal proteins according to the invention.

Preferably the lysosomal proteins have one or more paucimannosidic N-glycans comprising the structure of formula 1:

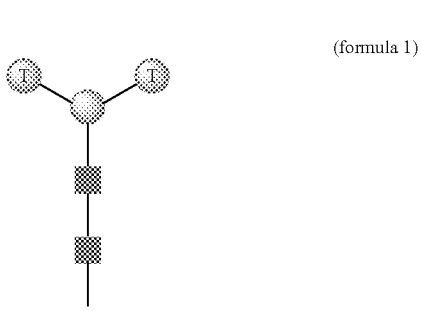

(formula 1)

wherein a square represents N-Acetylglucosamine (GlcNAc), a circle represents mannose (Man), and a circle with a T represents a terminal mannose. This formula 1, also referred herein as "MM" glycan, represents a core structure that may be further modified—in paucimannosidic N-glycans this further modification is also possible as long as the T-mannoses remain terminal, i.e. are at the non-reducing ends of the sugar chains. The terminal mannoses may be methylated, especially O-methylated. Common modifications are where one or more of the GlcNAc or Man subunits may be α(1,3-fucosylated, α1,6-fucosylated and/or β1,2-xylosylated. α(1,3-fucosylations and α1,6-fucosylatations are found commonly on the reducing GlcNAc. A β1,2-xylosylation is usually found at the non-terminal mannose (circle without T in formula 1). According to the invention, preferably a α1,3-fucosylation and/or β1,2-xylosylation is prevented or reduced due to the inhibition of the respective enzymes during manufacture as mentioned above. α1,6-fucosylation may or may not be present. It is uncommon in plants but may be achieved by introduction of a α1,6-fucosyltransferase into the expressing cell or plant. Preferably at least 10%, at least 20%, at least 30%, at least 40%, at least 50%, at least 60%, at least 70%, at least 80%, at least 85%, at least 90%, or at least 95%, of the N-glycans of the lysosomal proteins of the inventive compositions comprise or consist of the structure of formula 1 (molar %).

A paucimannosidic N-glycan structure of the invention can also be represented by formula (2):

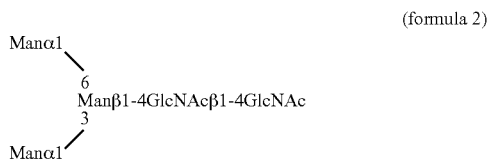

(formula 2)

Formula 2 further shows the type of carbohydrate subunit connectivity. The GlcNAc to the right is bound to the amino acid sequence of the lysosomal protein. The reducing and non-reducing ends of an oligosaccharide are conventionally drawn with the reducing-end monosaccharide residue furthest to the right and the non-reducing end furthest to the left (as e.g. in formula 2). Note, the reducing GlcNAc is shown left in the short formulas given herein, such as -GlcNAc$_2$-Man$_3$. In an N-glycan, the reducing -GlcNAc is bound to an Asparagine in the amino acid chain of the lysosomal protein. This is indicated by the left "-" being a bond to the Asn residue. In paucimannosidic glycoforms, two non-reducing mannose termini exist (left in formula 2, up in formula 1).

Formula (2) is the common core of most N-glycans, including high-mannose and complex N-glycans (see Rayon et al., J Exp. Botany, 1998, 49(326): 1463-1472). In case of paucimannosidic structures, both upper and lower Man to the left as shown in formula (2) are terminal, whereas in high mannose and complex N-glycans at least one Man contains a further bond to another Man or GlcNAc. α1,3-Fucosylation, α1,6-fucosylation and/or β1,2-xylosylation of this core are optional. α1,3-Fucosylation and β1,2-xylosylation are common in plants unless the respective enzymes are inhibited (e.g. as shown in WO 2004/057002 or Cox et al., Nature Biotechnology 24(12), 2006: 1591-7).

Should the expressed lysosomal proteins have amounts of MGn glycans (one additional terminal N-acetylglucosamine at one terminal Man as shown in formula 2) or GG glycans (one additional terminal N-acetylglucosamine at each terminal Man as shown in formula 2), these MGn and GG glycans can be converted to the structures of formula 1 or 2 by treatment with beta-N-Acetylglucosaminidase. Beta-N-Acetylglucosaminidase treatment can be performed with any moss produced lysosmal protein to increase paucimannosidic glycans. Moss expressed α-Galactosidase A usually does not need beta-N-Acetylglucosaminidase since paucimannosidic glycans are naturally in high concentrations. Depending on culturing conditions, moss produced glucocerebrosidase and alpha-glucosidase may sometimes need beta-N-Acetylglucosaminidase treatment. Other methods to create the inventive glycosylated lysosomal proteins include expression in insects or insect cells, such as Sf9 cells, expression in glyco engineered yeast cells and expression in moss with a vacuolar targeting signal (although less preferred since the signal may be immunogenic in a mammalian patient). Any description herein of "moss produced" or "bryophyte produced" lysosomal proteins relates to the products obtainable by the production in moss, i.e. having the inventive paucimannosidic N-glycans in high amounts as described herein, irrespective of the actual method of manufacture. Any method of manufacture can be selected to produce the inventive products and "moss produced" or "bryophyte produced" also refers to these products on non-moss production methods. "Moss produced" or "bryophyte produced" is used to express the unique glycosylation pattern, that was found in moss and is defined herein particularly, e.g. in product claims and the description of such products herein.

A unique characteristic of the bryophyte N-glycosylation of the lysosomal proteins according to the inventive method is the presence of methylated hexoses (Hex), preferably methylated mannose (Man) in the inventive N-glycans. These methylated mannoses, if terminal, do not interfere with uptake of the inventive lysosomal proteins and can even enhance it. Preferably the glycosylation pattern of the inventive composition has at least 1%, more preferred at least 2%, at least 3%, or at least 4%, N-glycans of the formula GlcNAc$_2$-Hex$_2$-methyl-Hex, with Hex being preferably mannose (molar %). According to the inventive method, the methylation is usually a methylation of an oxygen of mannose, in particular a 2-O-methylation. These are preferred methylations of the inventive lysosomal proteins of the composition. Preferably, at least 1%, more preferred at least 2%, at least 3%, or at least 4%, of the N-glycans of the composition have a methylation, especially a O—, e.g. 2-O-methylation (molar %). Preferably in these methylated N-glycans, only one of the at least two terminal (non-reducing) mannoses is methylated.

Preferably the glycosylation pattern comprises the following N-glycans:
i) 0% to 35%, preferably 0.5% to 30%, -GlcNAc$_2$-(Man$_2$methyl-Hex);

ii) 30% to 80%, preferably 40% to 70%, especially preferred 45% to 60%, -GlcNAc$_2$-Man$_3$;
iii) 0% to 30%, preferably 4% to 22%, -GlcNAc$_2$-Man$_3$-GlcNAc;
iv) 0% to 15%, preferably 2% to 12%, -GlcNAc$_2$-Man$_3$-GlcNAc$_2$;
v) 0% to 5%, preferably 0% to 3%, -GlcNAc$_2$-Man$_3$-Hex$_2$;
vi) 0% to 11%, preferably 1% to 8%, -GlcNAc$_2$-Man$_3$-Hex$_3$;
vii) 0% to 10%, preferably 1% to 7%, -GlcNAc$_2$-Man$_3$-Hex$_4$;
viii) 0% to 10%, preferably 1% to 7%, -GlcNAc$_2$-Man$_3$-Hex$_5$;
wherein all of these compounds together amount to 100% or less than 100%, which is self-evident (all % are molar %). Less than 100% are possible since other N-glycans, not specified in the list above may be present. Such other N-glycans may be between 0% and 30%, preferably between 0.01% and 20%, especially preferred between 0.1% and 10%. Any one of the specified N-glycans i) to viii) may be in an amount of at least 0.01% instead of 0%. GlcNAc is a N-Acetylglucosamine subunit, Man is a mannose subunit, Hex is a hexose subunit, methyl-Hex is a methylated hexose subunit, preferably 2-O methyl hexose. In this glycosylation pattern -GlcNAc$_2$-(Man$_2$methyl-Hex) and -GlcNAc$_2$-Man$_3$ together amount to at least 45% (molar %), i.e. these are paucimannosidic N-glycans that contribute to this amount as mentioned in the summary of the invention. Especially preferred Hex is Man in any one of the above N-glycans i) to viii). The GlcNAc at the reducing end of the glycan may be fucosylated or is not fucosylated in any one of the above N-glycans i) to viii). A Man at a branching point is xylosylated or is not xylosylated in any one of the above N-glycans i) to viii).

In a particular preferred embodiment, all N-glycans listed above i) to viii) are in the preferred amount as given in the preceding paragraph.

Also preferred, the glycosylation pattern comprises N-glycan i), -GlcNAc$_2$-(Man$_2$methyl-Hex), in an amount of at least 0.5%, at least 1%, at least 2% or at least 3%. Especially preferred, it is in an amount of at most 30%, at most 25%, at most 20% or at most 15%. Its amount may be in the range 0.5% to 30%, 1% to 25% or 2% to 20%.

Also preferred, the glycosylation pattern comprises N-glycan ii), -GlcNAc$_2$-Man$_3$, in an amount of at least 30%, at least 40%, at least 45% or at least 50%. Especially preferred, it is in an amount of at most 80%, at most 75%, at most 70% or at most 65%. Its amount may be in the range 30% to 80%, 40% to 70% or 45% to 60%. This is the most important N-glycan according to the invention and may be present in these amounts in any embodiment of the invention.

Also preferred, the glycosylation pattern comprises N-glycan iii), -GlcNAc$_2$-Man$_3$-GlcNAc, in an amount of at least 0.5%, at least 2%, at least 4% or at least 6%. Especially preferred, it is in an amount of at most 30%, at most 25%, at most 20% or at most 15%. Its amount may be in the range 0.5% to 30%, 1% to 25% or 2% to 20%.

Also preferred, the glycosylation pattern comprises N-glycan iv), -GlcNAc$_2$-Man$_3$-GlcNAc$_2$, in an amount of at least 0.2%, at least 0.5%, at least 1% or at least 2%. Especially preferred, it is in an amount of at most 20%, at most 15%, at most 12% or at most 10%. Its amount may be in the range 0.5% to 15%, 1% to 12.5% or 2% to 10%.

Also preferred, the glycosylation pattern comprises N-glycan v), -GlcNAc$_2$-Man$_3$-Hex$_2$, in an amount of at least 0.01%, at least 0.05%, at least 0.1% or at least 0.5%. Especially preferred, it is in an amount of at most 5%, at most 4%, at most 3% or at most 2%. Its amount may be in the range 0.1% to 5%, 0.2% to 4% or 0.5% to 3%.

Also preferred, the glycosylation pattern comprises N-glycan vi), -GlcNAc$_2$-Man$_3$-Hex$_3$, in an amount of at least 0.1%, at least 0.2%, at least 0.75% or at least 1%. Especially preferred, it is in an amount of at most 11%, at most 10%, at most 8% or at most 6%. Its amount may be in the range 0.5% to 11%, 1% to 10% or 2% to 9%.

Also preferred, the glycosylation pattern comprises N-glycan vii), -GlcNAc$_2$-Man$_3$-Hex$_4$, in an amount of at least 0.1%, at least 0.2%, at least 0.3% or at least 0.4%. Especially preferred, it is in an amount of at most 10%, at most 8%, at most 6.5% or at most 5%. Its amount may be in the range 0.1% to 10%, 0.2% to 8.5% or 0.3% to 7%.

Also preferred, the glycosylation pattern comprises N-glycan viii), -GlcNAc$_2$-Man$_3$-Hex$_5$, in an amount of at least 0.1%, at least 0.2%, at least 0.3% or at least 0.4%. Especially preferred, it is in an amount of at most 10%, at most 8%, at most 6.5% or at most 5%. Its amount may be in the range 0.1% to 10%, 0.2% to 8.5% or 0.3% to 7%.

The inventive lysosomal proteins can be of any source, preferably mammalian, especially human or a non-human animal, such as a rodent, a dog, cat, horse, cow, camel, pig.

Plant produced glycoproteins, including the inventive bryophyte produced lysosomal proteins are usually not mannose phosphorylated. Also according to the invention, the N-glycans may be non-mannose phosphorylated, especially not phosphorylated at all. Phosphorylation can be done artificially by introducing a phosphorylating enzyme into the expressing cell or by phosphorylation after isolation of the protein from the cells. Thus, the lysosomal protein composition according to the invention comprises non-phosphorylated or phosphorylated lysosomal proteins. Preferably the amount of phosphorylated N-glycans of the lysosomal proteins of the composition is below 20%, especially preferred below 15%, below 10%, below 5%, below 2%, below 1%, or even below 0.5%, e.g. 0% (molar %).

The inventive lysosomal proteins may be PEGylated non-PEGylated. PEGylation may modify the solubility, bioavailability and in vivo half-life when administered to a patient. Given that half-life of the inventive paucimannosidicly glycosylated lysosomal proteins is reduced due to smaller N-glycan structure as compared to mammalian produced lysosomal proteins, PEGylation is especially preferred to compensate for this draw-back. Especially preferred is a reversible PEGylation, leading to a at least partial loss of the PEGylation in vivo, e.g. by introducing a hydrolysable bond, such as a Schiff base, so as not to interfere with cellular uptake. Also as a measure to reduce cellular uptake interference, the PEGylation can be of short PEG chains, such as PEG with 4 to 1000, preferably 8 to 100 or 10 to 50 subunits. Instead of PEG, any short hydrophilic polymer can be used to increase half-life, preferably with a molecular weight of less than 100 kDa, less than 10 kDa or less than 1 kDa. Preferably PEG has 2-200, preferably 3 to 100 or 4 to 50, glycol subunits. The lysosomatic protein can be PEGylated via a linking moiety as means for indirect attachment of the PEG molecule. Alternatively, also direct attachment is possible.

Preferably the inventive lysosomal proteins are non-crosslinked. Crosslinking can interfere with cellular uptake and stability and is less preferred. Preferably crosslinking is combined with PEGylation. For example, PEG can be used as cross-linking agent, especially in case of bi- or multi-functional PEG having at least two functional groups for binding to a protein, such as bis-COOH-PEG or bis-NHS- PEG. PEGylation can mask the negative aspects of cross-linking that cause interference with cellular uptake and stability.

Crosslinking can lead to the formation of multimeric lysosomal proteins, especially preferred dimeric lysosomal proteins, as e.g. described for alpha-galactosidase is WO 2011/107990 (incorporated herein by reference). In cross-linked proteins, at least two lysosomal proteins are connected either directly or indirectly via a linking moiety.

Cross-linking and/or PEGylation can be by linking moiety. for example, the linking moiety is optionally a moiety which is covalently attached to a side chain, an N-terminus or a C-terminus, or a moiety related to post-translational modifications (e.g., a saccharide moiety) of an lysosomal protein monomer, as well as to a side chain, an N-terminus or a C-terminus, or a moiety related to post-translational modifications (e.g., a saccharide moiety) of another lysosomal protein monomer. Exemplary such linking moieties are described in detail hereinunder.

Alternatively, the linking moiety forms a part of the lysosomal protein monomers being linked (e.g., a part of a side chain, N-terminus or C-terminus, or a moiety related to post-translational modifications (e.g., a saccharide moiety) of an lysosomal protein monomer, as well as of a side chain, an N-terminus or a C-terminus, or a moiety related to post-translational modifications (e.g., a saccharide moiety) of another lysosomal protein monomer). Thus, for example, the linking moiety can be a covalent bond (e.g., an amide bond) between a functional group of a side chain, N-terminus, C-terminus or moiety related to post-translational modifications of a monomer (e.g., an amine), and a complementary functional group of a side chain, N-terminus, C-terminus or moiety related to post-translational modifications of another monomer (e.g., carboxyl), wherein such a covalent bond is absent from the native form of the α-galactosidase. Other covalent bonds, such as, for example, an ester bond (between a hydroxy group and a carboxyl); a thioester bond; an ether bond (between two hydroxy groups); a thioether bond; an anhydride bond (between two carboxyls); a thioamide bond; a carbamate or thiocarbamate bond, are also contemplated. Optionally, the linking moiety is devoid of a disulfide bond. However, a linking moiety which includes a disulfide bond at a position which does not form a link between monomers (e.g., cleavage of the disulfide bond does not cleave the link between the monomers) is within the scope of this embodiment of the invention. A potential advantage of linking moiety devoid of a disulfide bond is that it is not susceptible to cleavage by mildly reducing conditions, as are disulfide bonds. Optionally, the linking moiety is a non-peptidic moiety (e.g., the linking moiety does not consist of an amide bond, an amino acid, a dipeptide, a tripeptide, an oligopeptide or a polypeptide). Alternatively, the linking moiety may be, or may comprise, a peptidic moiety (e.g., an amino acid, a dipeptide, a tripeptide, an oligopeptide or a polypeptide). Optionally, the linking moiety is not merely a linear extension of any of the lysosomal protein monomers attached thereto (i.e., the N-terminus and C-terminus of the peptidic moiety is not attached directly to the C-terminus or N-terminus of any of the lysosomal protein monomers). Alternatively, the linking moiety is formed by direct covalent attachment of an N-terminus of a lysosomal protein monomer with a C-terminus of another lysosomal protein monomer, so as to produce a fused polypeptide. Such a polypeptide will not be a native form of α-galactosidase, although it may comprise two lysosomal protein monomers essentially in their native form. However, the covalent linking of α-galactosidase monomers described herein is preferably in a form other than direct linkage of an N-terminus to a C-terminus. The linking moiety is preferably a small moiety of 10 to 1000 Da, preferably 20 to 500 Da.

In cross-linking and/or PEGylation, the linking moiety may comprise one or more reactive group for binding to the lysosomal protein. Such reactive groups may react for example with a thiol group or react with an amine group to form an amide bond. As used herein, the phrase "reactive group" describes a chemical group that is capable of undergoing a chemical reaction that typically leads to a bond formation. The bond, according to the present embodiments, is preferably a covalent bond (e.g., for each of the reactive groups). Chemical reactions that lead to a bond formation include, for example, nucleophilic and electrophilic substitutions, nucleophilic and electrophilic addition reactions, alkylations, addition-elimination reactions, cycloaddition reactions, rearrangement reactions and any other known organic reactions that involve a functional group, as well as combinations thereof. The reactive group may optionally comprise a non-reactive portion (e.g., an alkyl) which may serve, for example, to attach a reactive portion of the reactive group to a linking moiety (e.g., poly(alkylene glycol) or analog thereof) described herein. The reactive group is preferably selected so as to enable its conjugation to the lysosomal protein. Exemplary reactive groups include, but are not limited to, carboxylate (e.g., —$CO_2H$), thiol (—SH), amine (—$NH_2$), halo, azide (—$N_3$), isocyanate (—NCO), isothiocyanate (—N=C=S), hydroxy (—OH), carbonyl (e.g., aldehyde), maleimide, sulfate, phosphate, sulfonyl (e.g. mesyl, tosyl), etc. as well as activated groups, such as N-hydroxysuccinimide (NHS) (e.g. NHS esters), sulfo-N-hydroxysuccinimide, anhydride, acyl halide (—C(=O)-halogen) etc. In some embodiments, the reactive group comprises a leaving group, such as a leaving group susceptible to nucleophilic substitution (e.g., halo, sulfate, phosphate, carboxylate, N-hydroxysuccinimide).

The invention also provides the inventive lysosomal protein or composition as a medicament. Further provided is a method of treatment of a lysosomal storage disease comprising administering a lysosomal protein composition to a patient, e.g. a mammal. Related thereto, the invention provides the inventive lysosomal protein for use in the treatment of a lysosomal storage disease. The patient can be a mammalian, especially human or a non-human animal, such as a rodent, a dog, cat, horse, cow, camel, pig. Preferably the lysosomal protein is from the same species as the patient in order to prevent immunoreactions against the proteins amino acid chain.

Preferably the disease and lysosomal protein are selected from the following table:

| disease | lysosomal protein |
| --- | --- |
| Fabry Disease | α-Galactosidase A (GLA) |
| Gaucher's Disease | β-Glucoceramidase, β-glucosidase (glucocerebrosidase) |
| Alpha-Mannosidesis | α-Mannosidase |
| Aspartylglucosaminuria | Aspartylglucosaminidase |
| Beta-Mannosidosis | β-Mannosidase |
| Farber Disease | Acid Ceremidase |
| Fucosidosis | α-Fucosidase |
| GM1-Gangliosidosis | β-Galactosidase, β-Hexosaminidase activator protein |
| Krabbe Disease | Galactocerebrosidase; Galactoceramidase |

-continued

| disease | lysosomal protein |
|---|---|
| Lysosomal Acid Lipase (LAL) Deficiency | lysosomal acid lipase (LAL) |
| Mucopolysaccharidoses (MPS, Type I-IX) | |
| MPS I | α-Iduronidase |
| MPS II | Iduronate-2-sulfatase |
| MPS IIIA | Glucosamine-N-sulfatase; Heparansulfatsulfamidase (SGSH) |
| MPS IIIB | α-N-acetyl-glucosaminidase (NAGLU) |
| MPS IIIC | α-glucosaminide-N-acetyltransferase |
| MPS IIID | N-Acetygalactosamine-6-sulfatase |
| MPS IVA | Galactose-6-sulfate sulfatase |
| MPS IVB | β-Galactosidase |
| MPS VI | N-Acetygalactosamine-4-sulfatase |
| MPS VII | β-Glucoronidase |
| MPS IX | Hyaluronidase |
| Niemann Pick Disease | Sphingomyelinase |
| Pompe Disease | (Acid) alpha-1,4-glucosidase |
| Sandhoff Disease | β-Hexosaminidase, or its α subunit |
| Schindler Disease | Alpha-N-acetylgalactosaminidase (NAGA); α-Galactosaminidase |
| Tay-Sachs Syndrome | β-Hexosaminidase A |
| Sialidosis | Neuraminidase |

The dosis for administration is preferably a dosis of 0.05 to 100 mg/kg body weight, preferably of 0.1 to 50 mg/kg body weight, especially preferred of 0.3 to 10 mg/kg body weight, such as 0.3, 1 or 3 mg/kg body weight.

Since there is no cure for lysosomal storage diseases a chronic treatment is required with repeated administrations of the enzyme replacement in regular intervals. Preferably the inventive lysosomal protein is administered at an interval of 1 to 30 days, preferably of 2 to 25 days, more preferred of 3 to 23, or even of 4 to 22 days, of 5 to 21 days, of 6 to 20 days, of 7 to 19 days, of 8 to 18 days, of 9 to 17 days, of 10 to 16 days, or of 11 to 15 days. Especially preferred are 14 day intervals. Administration in such intervals allows steady enzyme activity in the cells lysosomes, countering protein clearance.

The lysosomal proteins may be administered by any route that leads to a functional enzyme reaching the vascular system, especially the blood stream. Preferred is intravenous (i.v.) infusion. Further routes of administration include intraperitoneal (i.p.), intramuscular (i.m.) and subcutaneous (s.c.) administration. I.p., i.m. and s.c. administration routes may lead to reduced distribution of the lysosomal protein in the target tissue (like heart, kidney, liver and spleen), still sufficient amounts can be administered to these tissue via these routes. These non. i.v. routes, in particular i.p., i.m. and s.c., benefit from better patient acceptance and usually the benefit outweighs the reduced target tissue distribution. Furthermore, pharmacokinetic profiles of the non-i.v. administrations are beneficial as the therapeutic enzyme is available in patients plasma over a prolonged time period.

In preferred embodiments, the inventive medical treatment with a lysosomal protein of the invention (bryophyte produced) is in combination with a lysosomal protein of the same type and qualitative enzymatic activity but produced in non-plant, especially mammalian or fungal, cells. The non-plant produced lysosomal protein may have phosphorylated mannose for mannose-6-phosphate receptor (M6PR) recognition and cellular uptake. Also, a lysosomal protein with (artificially) phosphorylated mannose of any source may be used in combination with the inventive lysosomal protein. Such phosphorylated or non-bryophyte lysosomal proteins are already in use, such as Agalsidase alfa (Replagal®) and Agalsidase beta (Fabrazyme®) in case of alpha-galactosidase suitable for treatment of Fabry Disease; Alglucerase (Ceredase®), Imiglucerase, Velaglucerase alfa (VPRIV), as β-glucocerebrosidases, suitable for treatment of Gaucher Disease; Alglucosidase alfa (Myozyme®) suitable for the treatment of Pompe Disease; Idursulfase (Elaprase®), a lysosomal enzyme iduronate-2-sulfatase suitable for treatment of Hunter syndrome (MPS-II). Also possible are other plant produced lysosomal proteins to be used in combination, such as Taliglucerase alfa (Elelyso®), a glucocerebrosidase. The phosphorylated and/or non-bryophyte lysosomal protein may be cross-linked with the paucimannosidic lysosomal protein. The cross-linked di- or multimer is preferably further PEGylated. This improves stability, half-life and uptake.

The inventive lysosomal protein with paucimannosidic glycosylation can also be combined with a chaperon, in particular a specific or non-specific chaperon of the lysosomal protein of the same type and qualitative enzymatic activity. A pharmacologic chaperon of lysosomal proteins is e.g. 1-Deoxygalactonojirimycine (Migalastat). The chaperon is capable to modify re-establish some activity of a dysfunctional endogenous lysosomal protein in a lysosomal storage disease. The endogenous lysosomal protein can, and usually is, a phosphorylated lysosomal protein and can complement receptor interaction of the inventive paucimannosidic lysosomal protein—as described above for combination therapies for administrations of the phosphorylated or non-bryophyte protein. Without being limited to a specific therapy, it seems the chaperone can restore or increase enzymatic activity of the lysosomal protein, which has impaired activity due to a mutation causing the lysosomal storage disease. Especially preferred, Migalastat is used in combination with an inventive paucimannosidic or bryophyte produced alpha-galactosidase and/or used in the treatment of Fabry Disease.

The combination with phosphorylated or non-bryophyte lysosomal enzymes, especially those with M6PR recognition due to phosphorylation, complements uptake activity of the inventive enzymes, allowing to reach all therapeutically relevant cells with increased efficiency and a broader therapeutic scope of application.

The present invention is further illustrated by the following figures and examples without being limited to these embodiments of the present invention. Any element of the examples can be combined with the inventive concepts as described above.

FIGURES

FIG. 1: Linearized expression cassette for lysosomal protein expression (protein sequence: GLA) expression FIG. 2: Intermediate and final results of a typical purification of α-gal A (silver-stained SDS-PAGE)

FIG. 3: Purification of glucocerebrosidase from culture supernatant (Coomassie-stained SDS-PAGE)

FIG. 4: Purification of alpha-glucosidase from culture supernatant. Coomassie-stained SDS-PAGE of concentrated eluate from ConA-chromatography. A) moss-GAA eluate versus alglucosidase alfa (Myozyme). B) moss-GAA eluate versus Molecular Weight Standard.

Figure 5:
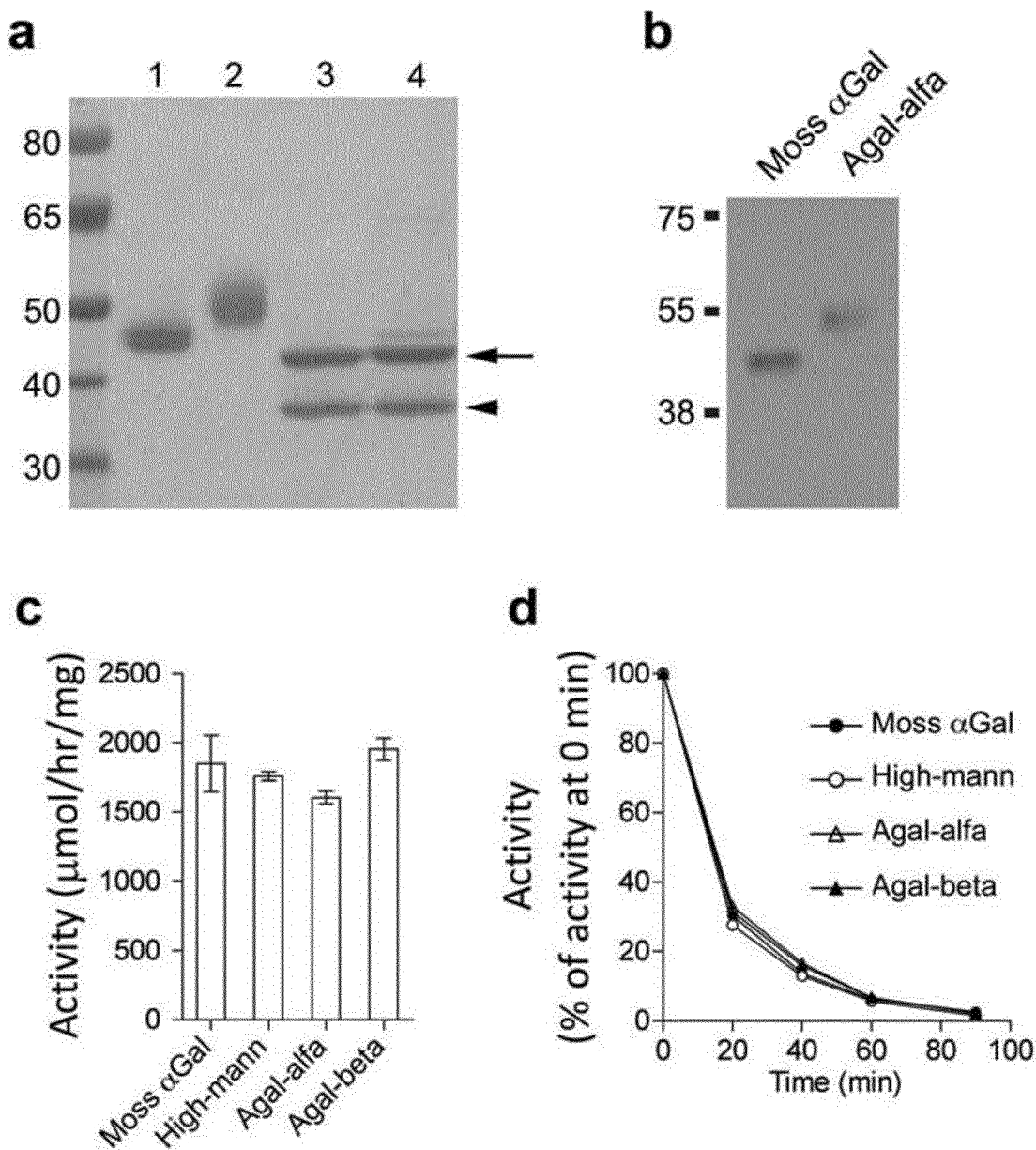

FIG. 5: In vitro characterization of the enzymes. (a) Enzyme preparations separated in SDS-PAGE and stained with Coomassie Blue. Lanes 1 and 2 are moss-aGal and agalsidase alfa respectively. Lanes 3 and 4 are moss-aGal and agalsidase alfa digested with PNGase F. Arrow, α-gal A enzymes after digestion; arrowhead, PNGase F (36 KDa). Protein standard and molecular weights are shown on left. (b) Moss-aGal and agalsidase alfa (1 ng each) detected by Western blot using a polyclonal antibody specific to human α-gal A. Representative data from 3 independent experiments was shown. (c) Specific α-gal A activities of enzyme preparations determined using artificial substrate 4-MU-α-D-galactopyranoside. Protein concentrations were measured by BCA assay. (d) Stability of the enzymes diluted in buffered human plasma and heated at 37° C. (data are means of triplicates). High-mann: high-mannose aGal; moss-aGal: α-galactosidase from moss; Agal-alfa: agalsidase alfa; Agal-beta: agalsidase beta.

Figure 6:
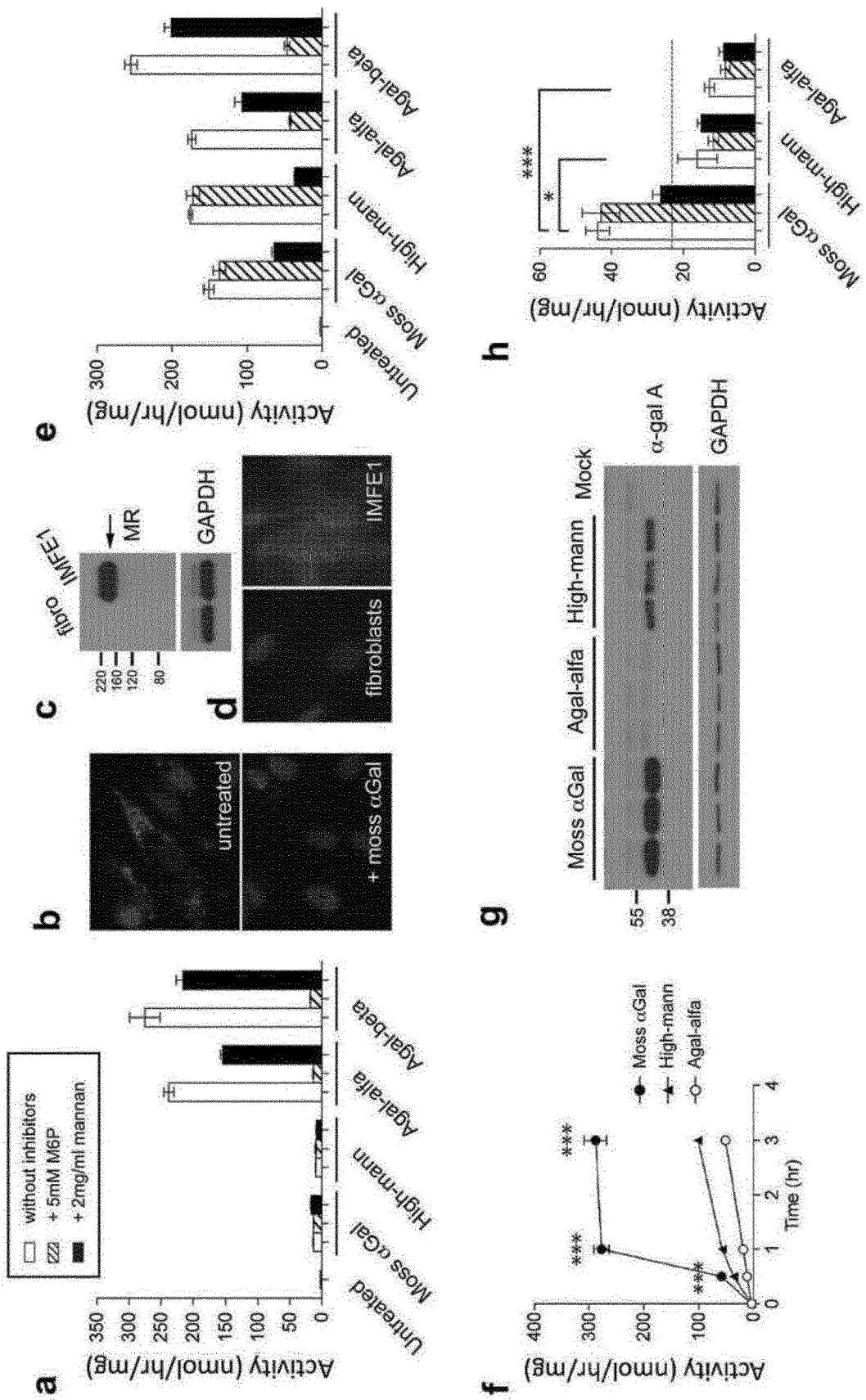

FIG. 6: In vitro uptake study. (a) Intracellular α-gal A activities of Fabry patient's fibroblasts (DMN96.125) after overnight incubation with different enzymes in the presence or absence of 5 mM M6P or 2 mg/ml yeast mannan. (b) $Gb_3$ immunofluorescence staining shows massive lysosomal accumulation of $Gb_3$ in untreated Fabry patient's fibroblasts (upper) and significantly decreased $Gb_3$ in the cells that were treated with moss-aGal (lower). (c and d) MR expression in Fabry patient's fibroblasts and microvascular endothelial cells IMFE1. IMFE1 cells were MR-positive determined by both western blot (c) and immunofluorescence staining (d), while the fibroblasts were MR-negative. (e) Intracellular α-gal A activities of IMFE1 cells after overnight incubation with different enzymes in the presence or absence of 5 mM M6P or 2 mg/ml yeast mannan. (f) Uptake rates of different enzymes in IMFE1 cells. Cells were harvested at indicated time points and intracellular activities were measured. ***$P<0.001$, moss-aGal vs. high-mann aGal or agalsidase alfa. (g) Western blot analysis of internalized α-gal A in IMFE1 cells after 3 hours incubation with different enzyme preparations. (h) Binding of different enzymes to IMFE1 cell. After 3 hours incubation at 4° C., cell surface-bound enzymes were determined by enzyme assay. The dotted line indicates activity level of mock-treated IMFE1 cells in this assay (i.e., background level). *$P<0.05$, ***$P<0.001$. All the data in graphs are presented as mean±SEM (n=3-4).

Figure 7:
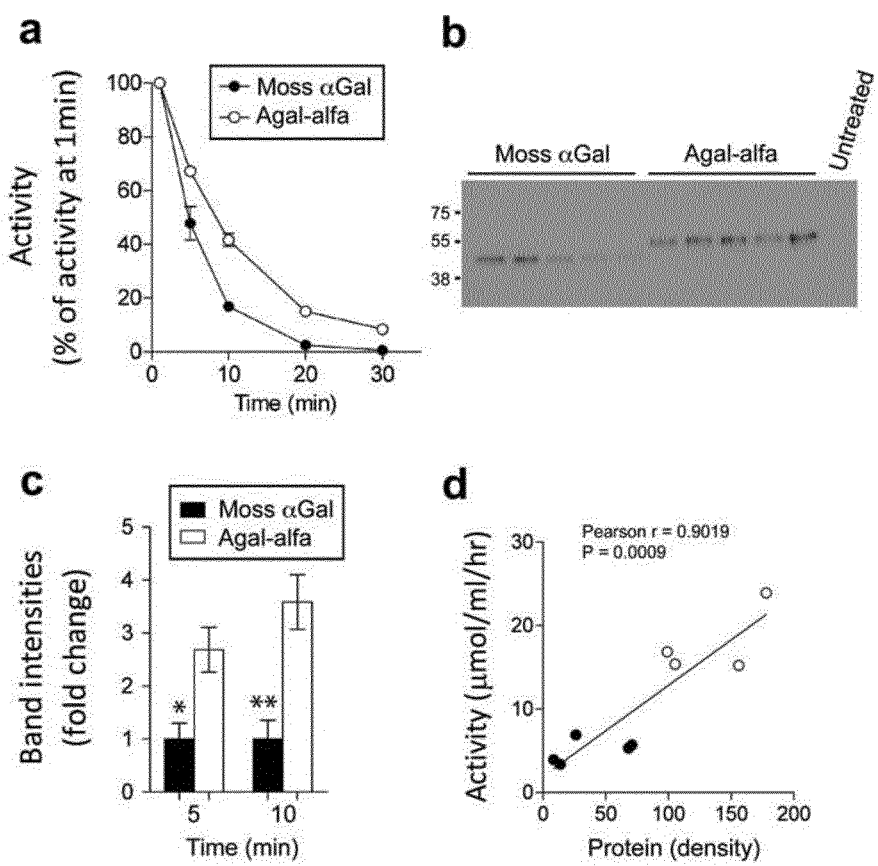

FIG. 7: Plasma pharmacokinetics. (a) Plasma clearance of infused moss-aGal and agalsidase alfa analyzed by enzyme activities. (b) Western blot for α-gal A in plasma at 10 min after infusion. (c) α-gal A protein amounts in plasma at 5 and 10 min after infusion; western blot bands intensities were analyzed by densitometry. (d) Correlation between α-gal A protein amounts and enzymatic activities in plasma at 10 min after injection. Data in (a) and (c) are presented as mean±SEM (n=4-5). *$P<0.05$, **$P<0.01$.

Figure 8:
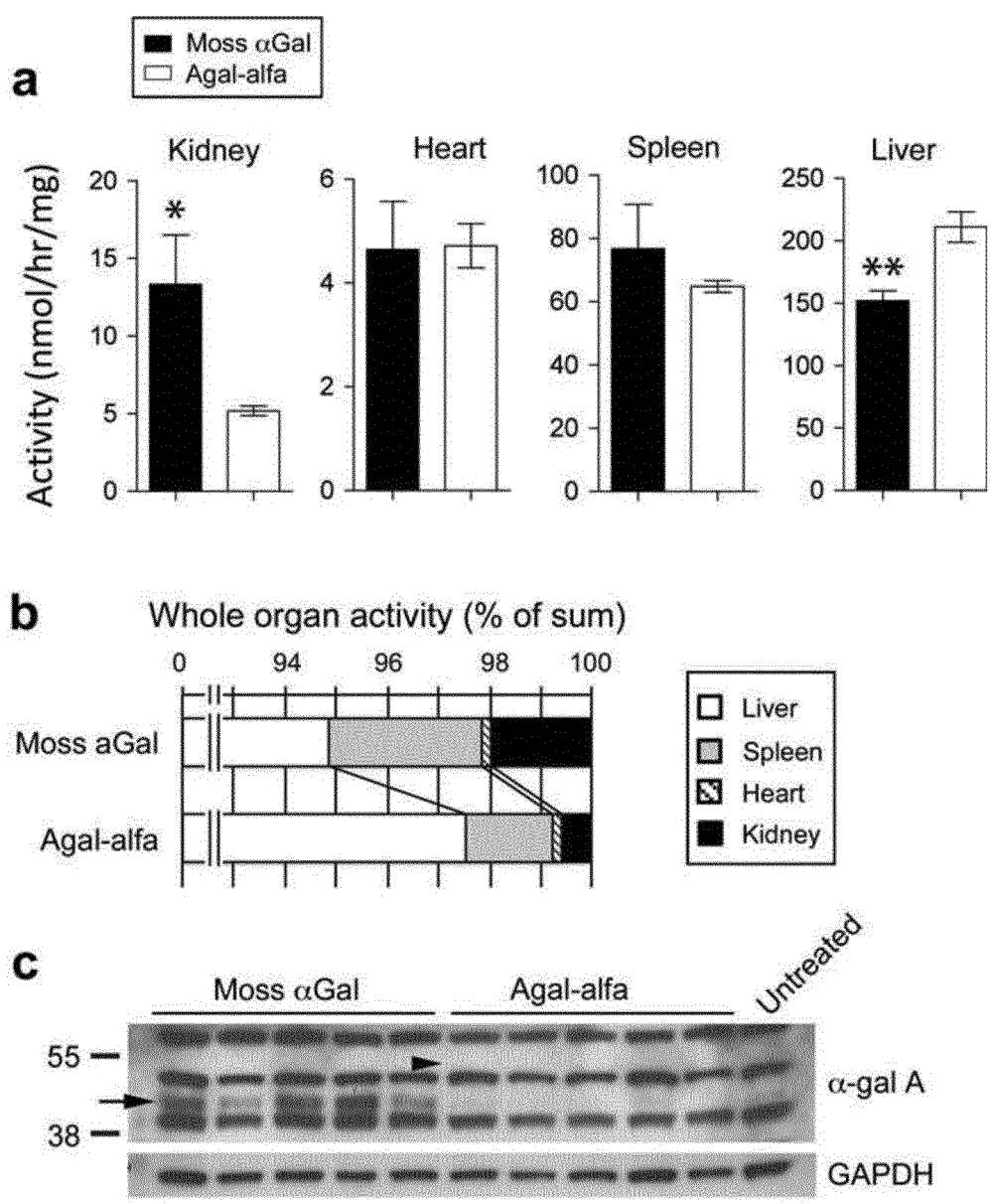

FIG. 8: Tissue distribution of infused enzymes. Enzyme preparations were injected into Fabry mice, and α-gal A activities in the kidney, heart, spleen and liver were measured 2 hours post-injection. (a) Specific activities in organs. Data are presented as mean±SEM (n=5). *$P<0.05$, **$P<0.01$. (b) Activities in whole organs were calculated and data are presented as % of total activity recovered from 4 organs. (c) α-gal A protein in kidney homogenates detected by western blot. Arrow, specific α-gal A band in moss-aGal-injected mice. No detectable specific band was seen in agalsidase alfa-injected mice. Arrowhead, approximate position where agalsidase alfa band may migrate to (based on findings shown in FIGS. 2b, 4b).

Figure 9:
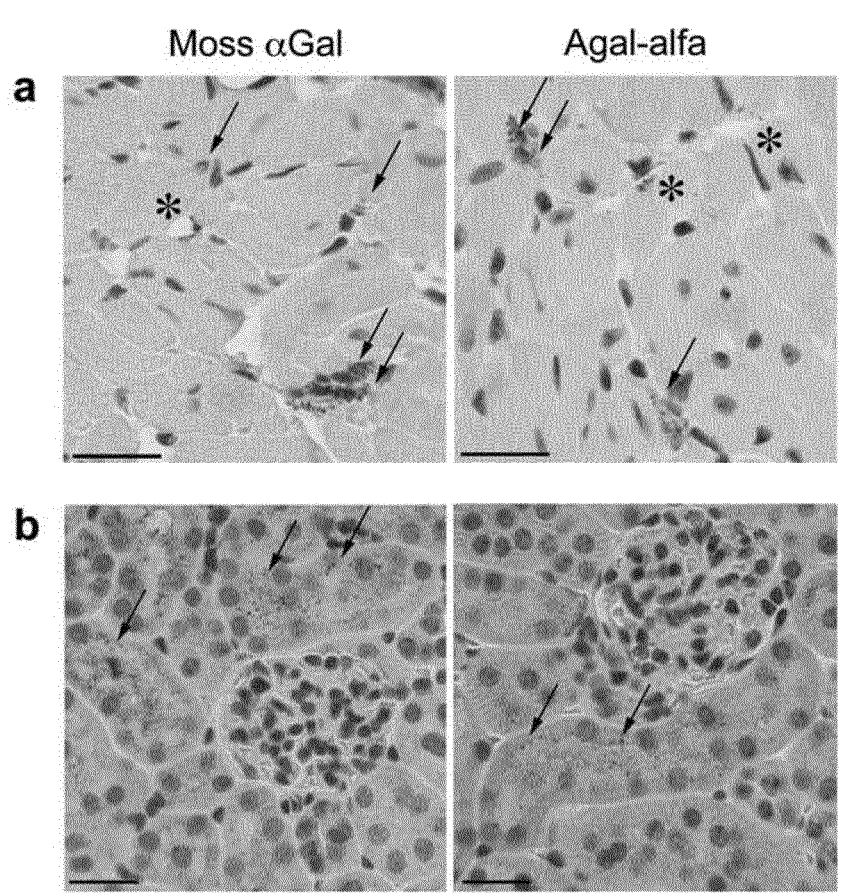

FIG. 9: Cellular localization of infused moss-aGal and agalsidase alfa. Cellular distribution of infused enzymes in the heart and kidney was determined by immunohistochemistry (n=2). Representative pictures were shown. (a) Heart. Asterisks indicate the blood vessels with immunostaining positive cells (most likely endothelial cells), and arrows indicate positive perivascular cells (presumably macrophages). (b) Kidney. Arrows indicate immunostaining positive tubular epithelial cells. Scale bar: 25 μm. Original magnification: 400×.

Figure 10:
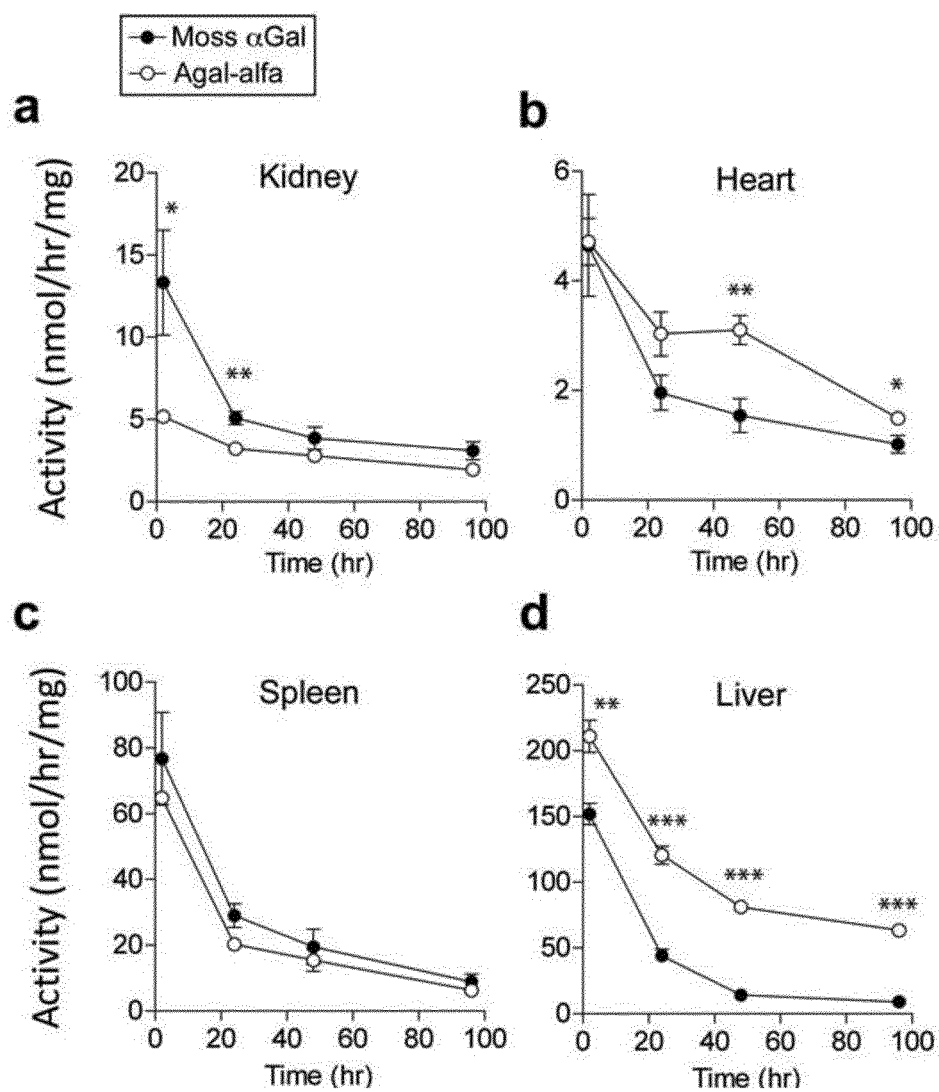

FIG. 10: Tissue kinetics of infused enzymes. Enzyme preparations were injected into Fabry mice, and α-gal A activities in kidney (a), heart (b), spleen (c) and liver (d) were measured at 2, 24, 48 and 96 hours post-injection. Data are presented as mean±SEM (n=4-5). *$P<0.05$, $P<0.01$, *$P<0.001$.

Figure 11:
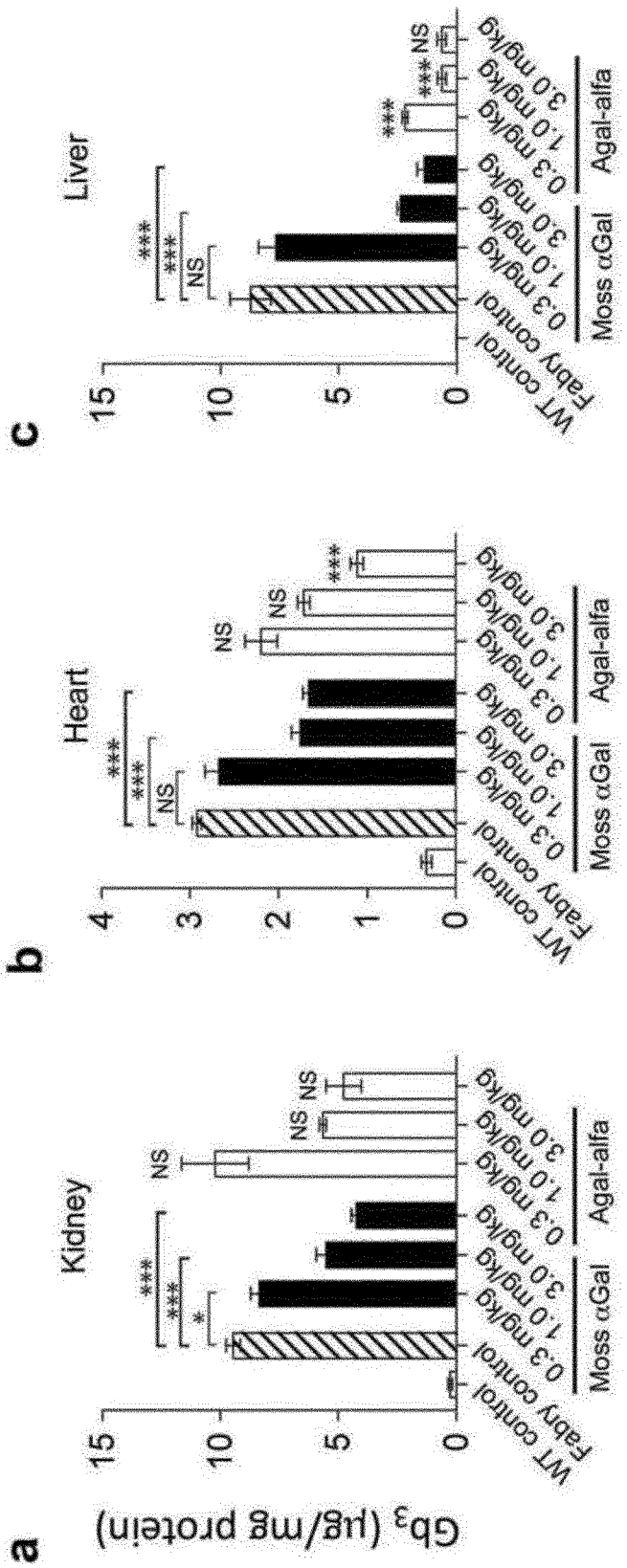

FIG. 11: Efficacy of moss-aGal in clearing accumulated $Gb_3$ in tissues. $Gb_3$ contents in kidney (a), heart (b) and liver (c) were analyzed 7 days after a single infusion of either moss-aGal or agalsidase alfa at various doses. Data are presented as mean±SEM (n=4-5). *$P<0.05$, ***$P<0.001$. Statistical significance shown on top of each agalsidase alfa-injected group indicates difference between agalsidase alfa and the same dose of moss-aGal.

Figure 12:
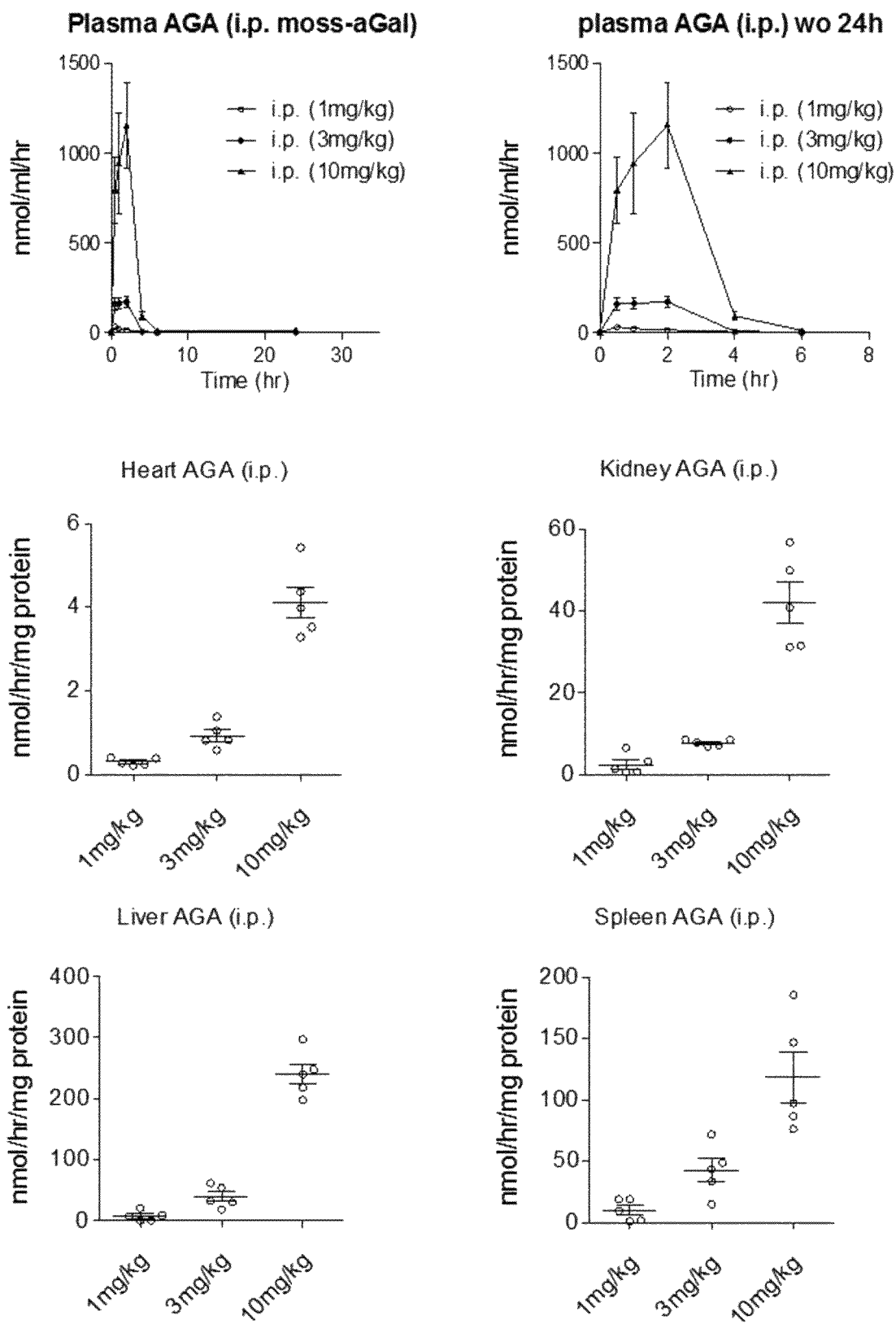
Figure 13:
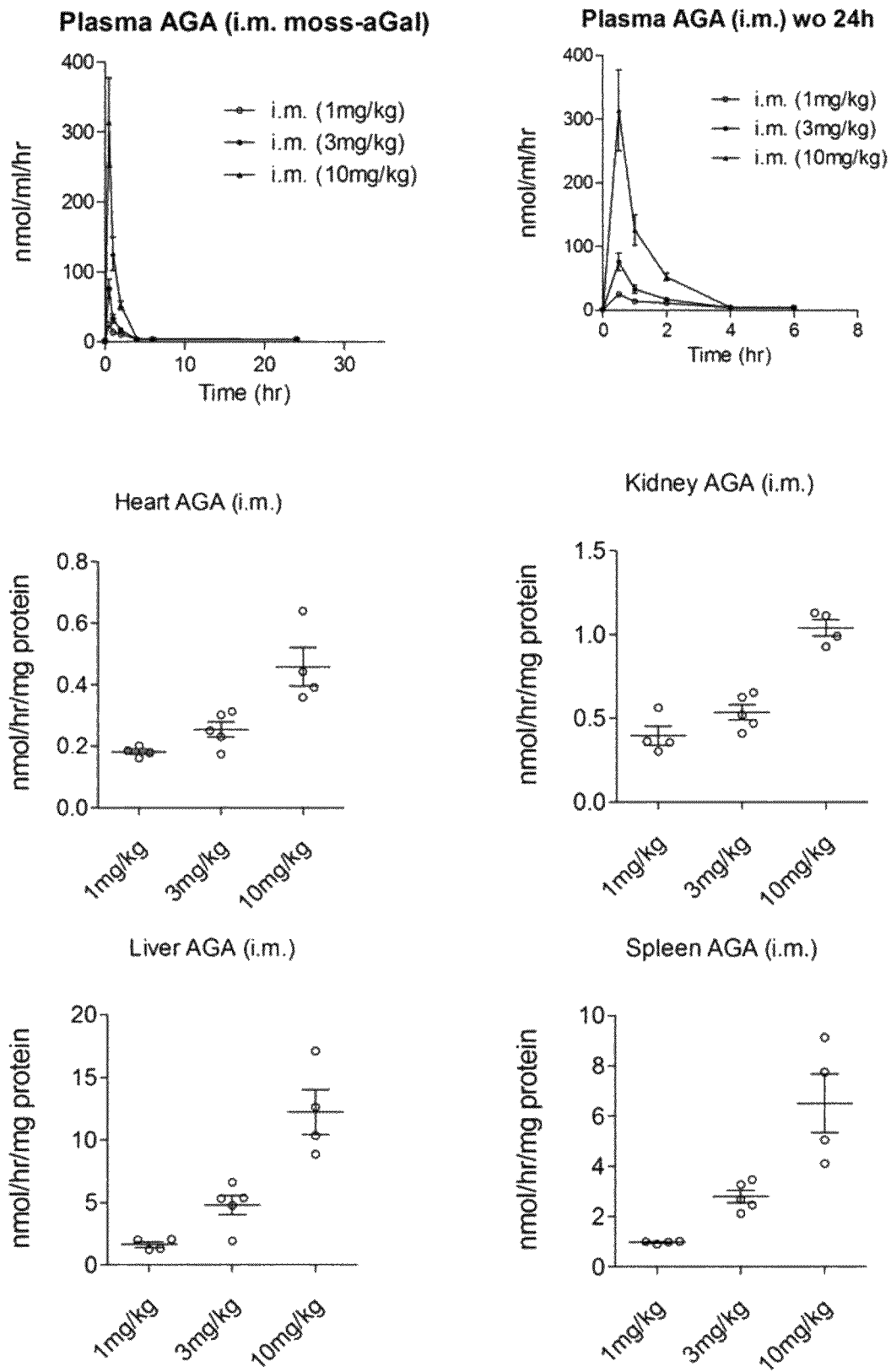
Figure 14:
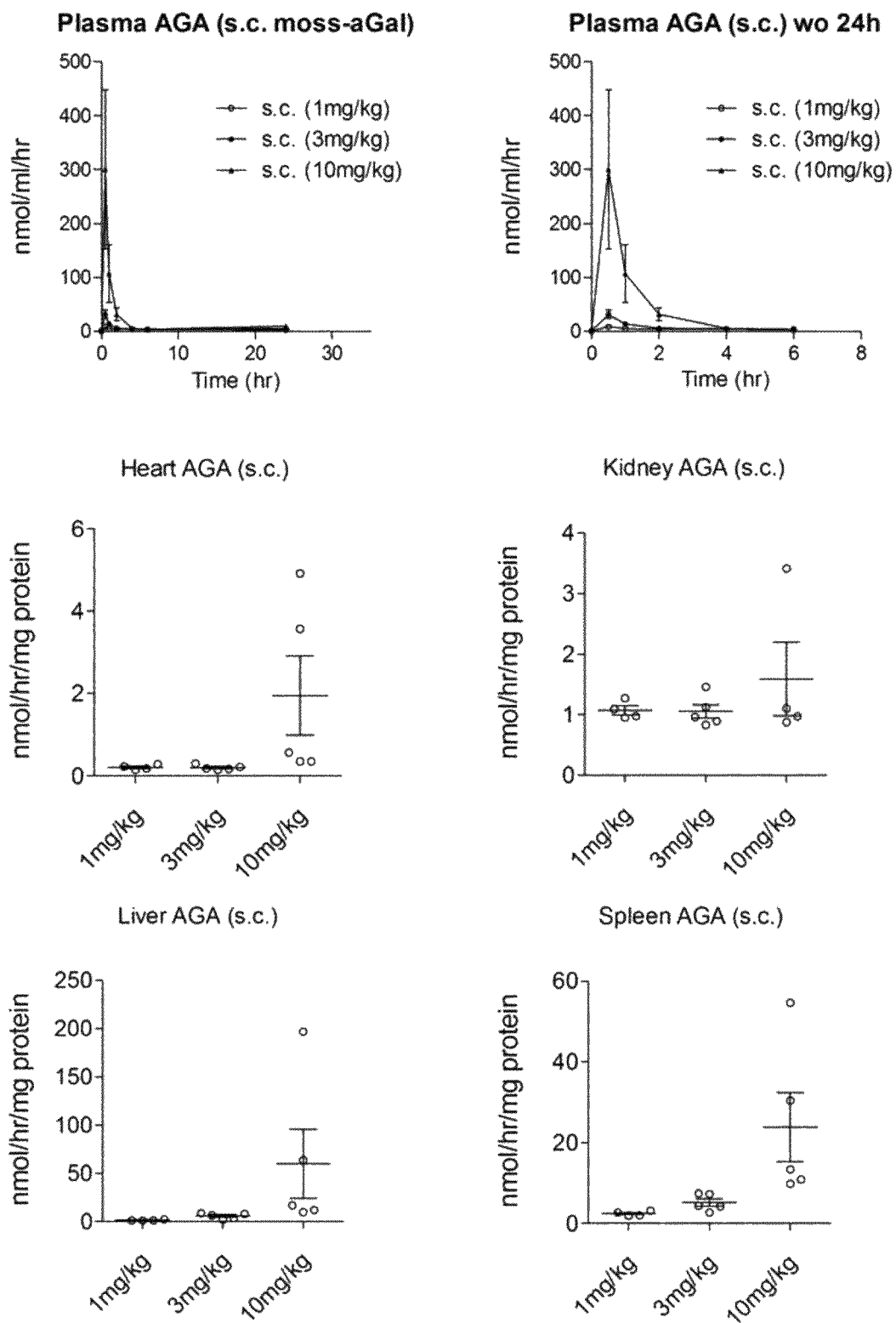

FIG. 12-14: Plasma and tissue activities for i.p. (FIG. 12), i.m. (FIG. 13) and s.c. (FIG. 14) administration.

EXAMPLES

Example 1: Production of Human Alpha-Galactosidase in Moss

Example 1.1: Expression Strain Construction

The DNA sequence of the human GLA gene (NCBI Reference Sequence: NM_000169.2) coding for alpha-galactosidase A (α-gal A) without native signal sequence (SEQ ID NO: 3) was synthesized as a codon-optimized version (SEQ ID NO: 4) and sub-cloned into a moss expression vector by GeneArt/Thermo Fisher Scientific (GENEART AG, Regensburg, Germany). Sequences harboring the α-gal A expression construct and a neomycin-resistance conferring gene (npt II) construct were excised as linear expression cassettes (FIG. 1) from the plasmids using restriction enzymes.

In order to generate stable α-gal A-producing moss cell lines, protoplasts of a moss double-knockout line devoid of plant specific α-1,3-fucose and β-1,2-xylose residues on its N-glycans (Koprivova et al. (2004) Plant Biotechnol. J. 2, 517-523; Weise et al. (2007) Plant Biotechnol. J. 5(3), 389-401; WO 2004/057002) were transformed with the purified expression cassettes in a PEG-based transformation procedure (Strepp et al. (1998) Proc. Natl. Acad. Sci. U.S.A 95, 4368). Transformed moss cells were regenerated and selected for resistance against the antibiotic G418. 2000 resistant moss plantlets were screened in two consecutive rounds for total α-gal A accumulation per biomass with the best strain becoming the standard production strain.

The linearized expression cassette comprises the following genetic elements: *Physcomitrella* actin promoter (P Actin) and 5' UTR, plant signal peptide (SP), cDNA sequence of human α-gal without native signal sequence (GLA), *Physcomitrella* tubulin 3' UTR, Cauliflower mosaic virus 35S promoter (P 35S), neomycin phosphotransferase gene (nptII) and Cauliflower mosaic virus 35S terminator (T 35S) (FIG. 1). The plant signal peptide contained the sequence MAFYKISSVFFIFCFFLIALPFHSYA (SEQ ID NO: 5).

The expression strain is a fully regenerated moss plant having the aGal-transgene stably integrated into its genome under the genetic control of moss derived regulatory elements.

Example 1.2: Enzyme Production

The α-gal A production strain was cultivated for 4 weeks (27 d) in a 20 L disposable bag (Cellbag 20, GE Healthcare, Germany) placed in a Wave™ Reactor Rocker (BioWave 20 SPS, Wave Biotech AG, Switzerland). The cultivation parameters were: 25-30 rpm rocking rate, 8° angle, SM07-medium (100 mM NaCl, 6.6 mM KCL, 2.0 mM $MgSO_4 \times 7H_2O$, 1.8 mM $KH_2PO_4$, 20.4 mM $Ca(NO_3)_2 \times 4H_2O$, 0.05 mM FeNa-EDTA, 4.9 mM MES, 0.1% (w/v) PEG4000, 100.26 μM $H_3BO_3$, 0.11 μM $CoCl_2 \times 6H_2O$, 0.1 μM $CuSO_4 \times 5H_2O$, 5 μM KI, 85.39 μM $MnCl_2 \times 4H_2O$, 1.03 μM $Na_2MoO_4 \times 2H_2O$, 0.11 mM $NiCl_2 \times 6H_2O$, 0.04 μM $Na_2SeO_3 \times 5H_2O$, 0.039 μM Zn-acetate$\times 2H_2O$), 25° C., 0.3 L$\times$ min$^{-1}$ pressured air supplemented with 2% to 4% $CO_2$ and illumination at 130 to 310 μE$\times$ m$^{-2}\times$ s$^{-1}$, 24 h light per day, delivered from light panels equipped with Osram FQ 24W 840 HO, Lumilux Cool White. The medium was additionally supplemented with 1000× Nitsch vitamin mixture (Nitsch vitamin mixture, Duchefa, Netherlands) according to manufacturer's instructions. The pH of the fermentation was controlled automatically at pH5-6 through titration with 0.5M $H_2SO_4$ and 0.5M NaOH with help of WAVEPOD I (GE Healthcare) in combination with Pump20 (GE Healthcare).

After the end of cultivation the culture broth underwent the following three step filtration cascade to deliver a moss free, clarified sterile filtrate: 1) moss harvest through cake filtration in customized PP filtration housing (Grosse et al. (2014) WO 2014/013045 A1) equipped with Zetaplus (01SP B3002, 3M, Germany), 2) depth filtration through a double layer Scale-Up Capsule (E0340FSA60SP03A, 3M, Germany) and 3) a final sterile filtration step (Millipore Express™ Plus, 0.22 μm, Millipore, Germany).

Figure 2:
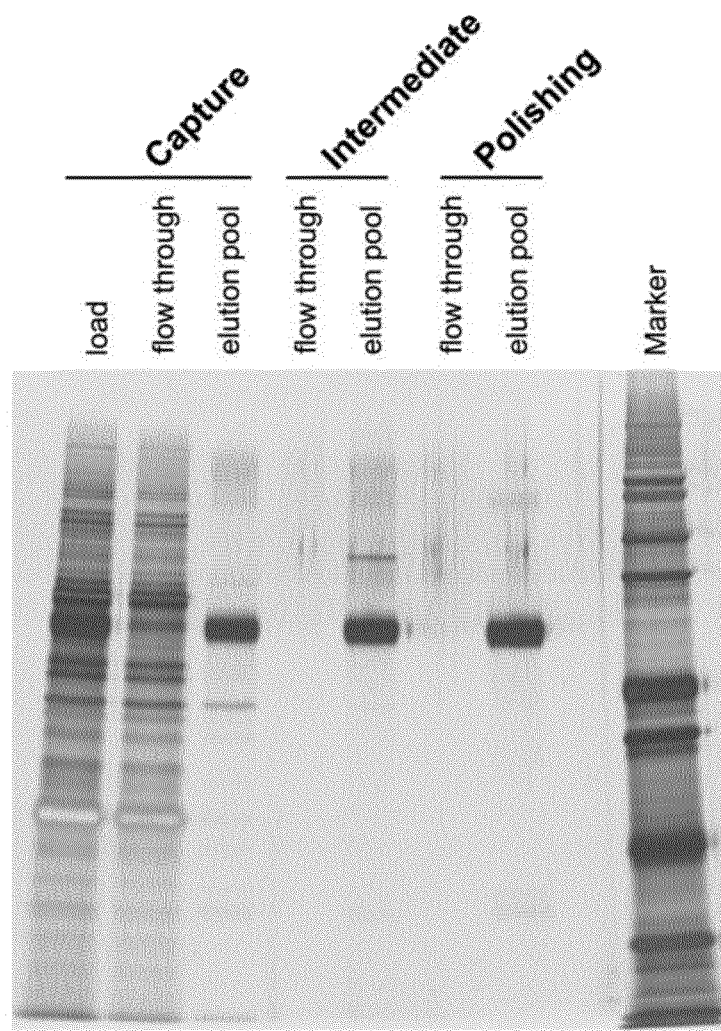

Subsequently the sterile filtrate was concentrated and buffer exchanged using tangential flow filtration (TFF) (Pall Centramate 500S, 30 kDa cutoff cellulose membrane). After a series of three chromatographic steps (Butyl-650M, DEAE, S) isolated α-gal A and high-mann α-gal A, respectively, were concentrated to approx. 0.5 mg/ml transferred into the formulation buffer and characterized. The enzyme was stored at ≤−65° C. until further use. Results of a typical purification process are depicted in FIG. 2.

Enzyme Activity Measurements:

α-gal A activity was measured by a fluorimetric assay using 5 mM 4-methylumbelliferyl-α-D-galactopyranoside at pH 4.4 in the presence of 0.1M N-acetylgalactosamine, a specific inhibitor of α-galactosidase B. Protein concentration was measured using BCA protein assay kit (Pierce) according to the suppliers instructions. The activity was expressed as μmol/mg protein/hour. Results are summarized in FIG. 5c.

SDS-PAGE Silver-Staining:

Samples were denatured in SDS sample buffer supplemented with reducing agent (Invitrogen) at 95° C. for 5 min. NuPAGE Bis-Tris 4-12% gels (Invitrogen) were used for protein separation. Silver-staining was done using Silver-Quest™ Staining Kit (Invitrogen) according to suppliers manual.

Host-Cell-Protein (HCP)-ELISA

To quantify remaining HCP levels in the purified α-gal A a novel HCP ELISA was developed (Biogenes GmbH, Germany). In short, a mock fermentation with the respective wild-type was done, media harvested and concentrated. The concentrated protein solution was used for immunization of rabbit. Total IgG were used to generate a sandwich ELISA for HCP quantitation. Results show a typical depletion of HCPs throughout the purification process by a factor of 10000.

Example 1.4: Summary of Production

Production of moss-aGal was accomplished in a photoautotrophic fermentation process in a 10 L-single-use disposable bag installed on a Wave™-rocker. The moss, grown in absence of any antibiotics, secreted moss-aGal into the purely mineral culture medium. Illumination of the culture bags was from the outside at an average photon flux of 200 μmol/m$^2$s. After having reached its final culture density, the moss was separated by cake filtration from the medium and the latter was clarified by a double layer depth filter system and final sterile filtration. The resulting cleared medium was concentrated and rebuffered by means of tangential flow filtration.

From this concentrated harvest, the enzyme was purified by a three step chromatographic approach, consecutively using a hydrophobic interaction (HIC)-, an anionexchange (AIE)- and a cationexchange (CIE)-column. Finally, the eluate from the last column was rebuffered and concentrated to 0.5 mg/ml.

The purification scheme provided pure moss-aGal (host cell protein (HCP) level ~100 ppm, single band on Coomassie SDS-Page, SE-HPLC purity 99%) with a typical yield of 30%.

Example 2: α-Galactosidase A Comparison

Example 2.1: Enzyme Production and Activity Assay

Paucimannosidic moss aGal was obtained as described in example 1. This production strain was additionally transformed with a knock-out construct targeting the sole *Physcomitrella patens* N-acetylglucosaminyltransferase I gene (Gnt I) to obtain production strains for high-mann aGal. To test the effect of increased number of terminal mannosyl residues on cellular uptake of the enzyme, α-gal A was also produced in a strain that was genetically depleted of its beta-1,2-N-acetylglucosaminyltransferase (GNT-I) activity. The knockout-modification results in an incapability of the moss to perform any complex-type glycan processing as all later enzymatic steps lack their substrate. Hence, alpha-mannosidase I mediated trimming in the cis-Golgi is the last processing-step and therefore all N-glycans of this strain are of the high-mannose type. Human alpha-galactosidase produced in this strain is referred to as high-mann aGal. Production and purification followed the same scheme as in example 1.

Mammalian cell produced Agalsidase alfa (Shire, Replagal®) and Agalsidase beta (Genzyme, Fabrazyme®) were obtained for comparative testing.

Cell pellets or Mouse tissues were lysed in ice-cold 0.2% Triton X-100 in saline. Lysates were centrifuged at 14,000 rpm for 15 min at 4° C., and the supernatants were used for enzyme assay. α-gal A activity was measured by the fluorimetric assay using 5 mM 4-methylumbelliferyl-α-D-galactopyranoside at pH 4.4 in the presence of 0.1M N-acetylgalactosamine, a specific inhibitor of α-galactosidase B. Protein concentration was measured using BCA protein assay kit (Pierce). The activity was expressed as nmol/mg protein/hour.

Example 2.2: Glycan Analysis

Glycan analysis of moss-aGal and Agalsidase alfa was done by Protagen Protein Services (Dortmund, Germany)

using HILIC-UPLC-MS. In short, N-glycans were released from the protein enzymatically using PNGase F. After cleanup and desalting isolated glycans were labeled using 2-aminiobenzamide (2-AB). Labeled glycans were separated on a ACQUITY UPLC BEH Glycan (2.1×100 mm) column using a linear gradient of 78% to 55.9% B (buffer A: 100 mM ammoniumformate pH4.5, buffer B: acetonitrile) in 38.5 min at 60° C. with a flow rate of 0.5 ml/min. Signals of eluting glycans were recorded by a fluorescence detector (excitation at 330 nm, emission at 420 nm). The assignment of fluorescence peaks to the respective glycans was done using recorded m/z values (Xevo-QTOF MS, Waters) and MasLynx software (Version 4.1, Waters).

Glycan analysis of high-mann aGal was performed as follows. About 25 µg of a-Gal was reduced (15 mM DTT), carbamidomethylated (55 mM iodoacetamide) and acetone precipitated (ace-tone:aqueous phase 4:1). The pellet was redissolved in 0.1 M ammonium bicarbonate buffer and digested for 12 h with either trypsin at 37° C. or chymotrypsin (both sequencing grade proteases, Roche, Mannheim).

About 3 µg of each digest was loaded on a BioBasic C18 column (BioBasic-18, 150×0.32 mm, 5 µm, Thermo Scientific) using 60 mM ammonium formate buffer as the aqueous solvent. A gradient from 3 to 75% acetonitrile was developed over 25 min at a flow rate of 6 µL/min. Detection was performed with a Waters QTOF Ultima mass spectrometer equipped with the standard ESI source in the positive ion mode. Data analysis was performed manually with MassLynx4.0.

TABLE 2

Glycan homogeneity/batch-to-batch stability

|  | Mammalian cell product (Replagal) | Moss product (moss-aGal) |
|---|---|---|
| No. of batches analyzed | 2 | 6 |
| No. of different N-glycans | 38 | 7 |
| Mean MAD (mean average deviation)* | 48% | 1.15% |

*Mean of all MADs within single glycoforms

Example 2.3: In Vitro Thermostability

Enzymes were diluted in plasma obtained from a healthy individual and were heated at 37° C. for indicated time lengths. To keep neutral pH, HEPES were added to the plasma at final concentration of 20 mM. After heating, α-gal A activities were measured.

Example 2.4: In Vitro Characterization

Moss-aGal had very uniform N-glycans with core-type $Man_3GlcNAc_2$ as dominant structure (FIG. 5). Carbohydrate chains of moss-aGal were almost exclusively constituted by mannose and GlcNAc, of which ~85% was mannose-terminated, ~10% had both mannose and GlcNAc terminal residues, and ~4% was GlcNAc-terminated (Table. 1). In comparison, $Man_5GlcNAc_2$ was the most abundant glycan structure in high-mann aGal (Table. 1) with some small

TABLE 1

N-glycan analysis results of Moss aGal and comparative enzymes

| Enzymes | Formula | Name | Terminal mannoses | Relative % or abundance |
|---|---|---|---|---|
| Moss aGal | HexNAc2 Hex2 methyl-Hex | Man3 + Methyl | 2 | 24% |
|  | HexNAc2 Hex3 | Man3 | 2 | 57% |
|  | (HexNAc2 Hex3) + HexNAc1 | Man3 + 1x NAc | 1 | 10% |
|  | (HexNAc2 Hex3) + HexNAc2 | Man3 + 2x NAc | 0 | 4% |
|  | (HexNAc2 Hex3) + (Hex)$_n$ | Man5-Man8 | 3 | 4% |
|  | Unidentified |  |  | 1% |
| High mann | (HexNAc2 Hex3) + Hex2 | Man5 | 3 | dominant |
|  | (HexNAc2 Hex3) + Hex1 | Man4 | 2 | few |
|  | (HexNAc2 Hex3) + Hex3 | Man6 | 3 | very few |
|  | (HexNAc2 Hex3) + Hex4 | Man7 | 3 | very few |
| Agalsidase alfa (Replagal ®) | (HexNAc2 Hex3) + Hex3 |  | 3 | 2% |
|  | (HexNAc2 Hex3) + Hex2 |  |  |  |
|  | (HexNAc2 Hex3) + HexNAc1 Hex2 |  | 2 | 4% |
|  | (HexNAc2 Hex3 Fuc1) + HexNAc1 |  | 1 | 1% |
|  | Phosphorylated glycans |  | 0 | 24% |
|  | 28 diverse complex/hybrid structures (each between 0.1% and 7%) |  | all 0 | 63% |
|  | Unidentified |  |  | 7% |

In view of glycan biochemistry, it can be assumed that HexNAc is N-acetylglucosamine and Hex is Mannose. Lines 1 and 2 of moss aGal, Man3 and Man3+Methyl represent paucimannosidic glycosylation. Surprisingly this fraction yielded about 80%. High mann and Agalsidase alfa represent comparative products.

As compared to Agalsidase alfa, moss aGal has a very homogeneous structure composition, with high batch consistency. High batch to batch consistency is a desired property to guarantee reproducibility and function expectation.

amount of $Man_4$, $Man_6$ and $Man_7$. As expected, there were no phosphorylated glycans in both moss-aGal and high-mann aGal. Agalsidase alfa showed highly heterogeneous glycan structures, of which ~24% were phosphorylated glycans, ~7% were mannose-terminated glycans and 63% were diverse structures (Table. 1).

In SDS-PAGE, moss-aGal was detected as a single major band with a faster mobility than agalsidase alfa (FIG. 5a), reflecting the lower carbohydrate content in moss-aGal. After removal of N-glycans by PNGase F, both moss-aGal and agalsidase alfa migrated to the same position (FIG. 5a).

High-mann aGal had similar mobility to that of moss-aGal. In western blot analysis, both moss-aGal and agalsidase alfa were detected by a polyclonal antibody to human α-gal A (FIG. 5b). With the same amount of protein loaded, the intensity of moss-aGal band in western blot was 2.14±0.58 times (n=3) of that of agalsidase alfa, likely due to the shorter sugar chains in moss-aGal that might facilitate the accessibility of the antibody to the epitope(s).

Specific activities of moss-aGal and high-mann aGal were similar to those of agalsidase alfa and agalsidase beta (FIG. 5c).

Moss-aGal and high-mannose moss-aGal had almost the same stability with agalsidase alfa or agalsidase beta when diluted in human plasma and heated at 37° C. (FIG. 2d).

Example 3: Production of Human Glucocerebrosidase in the Moss, Suitable for the Treatment of Gaucher Disease Example 3.1 Expression Strain Construction The cDNA sequence of the human GBA gene (Uniprot identifier P04062-GLCM_HUMAN, NCBI Reference Sequence: NM_000157.3) was synthesized and subcloned into a moss expression vector by GeneArt™ (Thermo Fisher Scientific, GENEART AG, Regensburg, Germany). The sequence used (SEQ ID NO: 7) is coding for human GBA (SEQ ID NO: 6) without the native annotated signal peptide (SP), which was replaced by a 26 aa plant SP (accurate cleavage is predicted with a score of 0.522 according to the SignalP4.1 web-tool). The GBA sequence was modified in one single base (base position 21 in SEQ ID 7, AAA→AA G) using an alternative codon for the amino acid lysine to facilitate cloning (avoiding an HindIII restriction site). Sequences harboring the GBA expression construct and a neomycin-resistance conferring gene (npt II) construct were excised as linear expression cassettes from the plasmids using restriction enzymes.

A moss cell line based on a double-knockout line devoid of plant specific α-1,3-fucose and β-1,2-xylose residues on its N-glycans as described in example 1.1 was used. In order to generate stable glucocerebrosidase-producing moss cell lines, protoplasts from this glyco-engineered basic cell line were transformed with the purified expression cassettes (FIG. 1) in a PEG-based transformation procedure as described in example 1.1. The linearized expression cassette comprises the same genetic elements as described in example 1.1 and FIG. 1, with the exception of using a human GBA sequence instead of the α-gal sequence (GLA). Transformed moss cells were regenerated and selected for resistance against the antibiotic G418. Around 700 resistant moss plantlets were screened in two consecutive rounds for total glucocerebrosidase accumulation per biomass with the best strain becoming the standard production strain. Human glucocerebrosidase produced in this strain is referred to as moss-GBA.

Example 3.2: Enzyme Production and Characterization

The same conditions and steps as described for example 1.2 and example 2 were used for production. The glucocerebrosidase was purified by tangential flow filtration with a 10 kDa cellulose cassette, cation exchange chromatography (CaptoS) for capturing and gel filtration (Sephadex) for polishing. Purified/enriched glucocerebrosidase is analysed by WesternBlotting, Coomassie/Silver stained SDS Page and enzyme activity assay. Purified enzyme was stored at −20° C. until further use. Purification steps are shown in FIG. 3. Similar high mannose-rich glycosylations were obtained. In a rerun, higher GlucNac terminated glycans were found of the form MGn and GnGn. Treatment with beta-N-Acetylglucosaminidase restored the high amount of paucimmanosidic glycan form distribution.

Example 3.3: Enzyme Assay

Activity of purified glucocerebrosidase is assessed by in vitro enzyme activity assay. Glucocerebrosidase was incubated in 60 mM Na-Citrat, 1.3 mM EDTA, 0.15% Triton-X100, 0.125% sodium taurocholate, 1 mM DTT, 2 mM 4-Nitrophenyl-beta-D-glucopyranoside, pH6 at 37° C. The reaction was stopped with 1M NaOH and the product formation was measured at spectroscopically at 405 nm.

Example 4: Production of Human Lysosomal Alpha-Glucosidase in the Moss, Suitable for the Treatment of Pompe Disease Example 4.1 Expression Strain Construction The cDNA sequence of the human GAA gene (Uniprot identifier P10253 (LYAG_HUMAN), NCBI Reference Sequence: NM_000152.4) was synthesized and sub-cloned into a moss expression vector by GeneArt™ (Thermo Fisher Scientific, GENEART AG, Regensburg, Germany). The sequence used (SEQ ID NO: 9) is coding for human GAA precursor (SEQ ID NO: 8) without the native annotated signal peptide (SP), which was replaced by a 26 aa plant SP (accurate cleavage is predicted with a score of 0.847 according to the SignalP4.1 web-tool) and a truncated pro-peptide. The GAA sequence was modified in one single base (base position 2484 in SEQ ID 9, ACG→ACA) using an alternative codon for the amino acid threonine to facilitate cloning (avoiding a PvuI restriction site). Sequences harboring the GAA expression construct and a neomycin-resistance conferring gene (npt II) construct were excised as linear expression cassettes from the plasmids using restriction enzymes.

A moss cell line based on a double-knockout line devoid of plant specific α-1,3-fucose and β-1,2-xylose residues on its N-glycans as described in example 1.1 was used. In order to generate stable alpha-glucosidase-producing moss cell lines, protoplasts from this glyco-engineered basic cell line were transformed with the purified expression cassettes (FIG. 1) in a PEG-based transformation procedure as described in example 1.1. The linearized expression cassette comprises the same genetic elements as described in example 1.1 and FIG. 1, with the exception of using a human GAA sequence (SEQ ID 9) instead of the α-gal sequence (GLA) and a different moss-promoter. Transformed moss cells were regenerated and selected for resistance against the antibiotic G418. Around 600 resistant moss plantlets were screened in two consecutive rounds for total alpha-glucosidase precursor accumulation per biomass with the best strain becoming the standard production strain. Human lysosomal alpha-glucosidase produced in this strain is referred to as moss-GAA.

Example 4.2: Enzyme Production and Characterization

The same conditions and steps as described for example 1.2 and example 2 were used for production. The alpha-glucosidase was purified by affinity chromatography using Con A Sepharose 4B. Alpha-glucosidase containing medium was mixed with the same volume of 50 mM sodium acetate, 1M NaCl pH5.2 to adjust for proper binding conditions and loaded onto the chromatography column. Elution was achieved by stepwise increase of concentration of α-D-methylglucoside. Purified/enriched alpha-glucosidase is analysed by WesternBlotting, Coomassie/Silver stained SDS Page and enzyme activity assay. Purified enzyme was stored at 4° C. or −20° C. until further use. SDS-PAGE analysis of enriched moss-GAA is shown in FIG. 4. Identity of band containing moss-GAA was confirmed by MS-analysis.

Alpha-glucosidase has 7 glycosylation sites, termed G1-G7. Glycoforms for each site were detected with MS/MS. The most in-tense peak for most sites (except GS2-GnM with 73%) was found to be that of the GnGn-glycoform. Therefore the enzyme preparation was treated with beta-N-Acetylglucosaminidase to cleave the terminal GlcNac to convert GnM and GnGn to paucimmanosidic glycans.

Example 5: Mannose Receptor-Mediated Delivery of Moss-Made α-Galactosidase A Efficiently Corrects Enzyme Deficiency in Fabry Disease Example 5.1: In Vitro Uptake Study Fabry patient-derived skin fibroblasts (DMN96.125) and endothelial cell line (IMFE1) were cultured in 10% FBS in DMEM and EGM-2MV (Lonza) respectively. Both cell lines have very low α-gal A activities, and have lysosomal $Gb_3$ accumulation that is detectable by immunostaining (Shen et al. (2008) *Mol Genet Metab* 95:163-168). The cells were incubated with α-gal A preparations (at final concentration of 10 µg/ml) in the presence or absence of 5 mM M6P or 2 mg/ml yeast mannan for indicated time lengths. After that, cells were harvested by trypsin treatment (0.25% trypsin/EDTA, 37° C.) that also eliminates extracellular α-gal A. After washing with PBS, the cell pellets were lysed for enzyme assay or western blot.

To test the ability of moss enzymes in degradation of accumulated $Gb_3$, DNN96.125 cells were incubated with α-gal A preparations (10 µg/ml) for 4 days with the medium replaced every 1-2 days. Mock-treated cells were used as untreated controls. $Gb_3$ was detected by immunostaining as described below.

Enzyme uptake study was performed in Fabry patients-derived fibroblasts with exogenous enzymes at a final concentration of 10 µg/ml. After 18 hours incubation, fibroblasts that were loaded with agalsidase alfa or agalsidase beta had markedly increased intracellular α-gal A activities (116- and 134-fold of activity of untreated cells respectively) (FIG. 6a). Uptake of these enzymes was nearly completely inhibited by M6P and was partially inhibited by yeast mannan, confirming that this uptake was predominantly through M6PR. Fibroblasts incubated with moss-aGal or high-mann aGal had a significantly lower increment of intracellular α-gal A activities (6.4- and 4.8-fold of untreated cells respectively) (FIG. 6a). Uptake of both moss-aGal and high-mann aGal was not inhibited by either M6P or mannan. This was consistent with little or no expression of MR in these cells (FIG. 6c,d). Despite the low uptake, lysosomal accumulation of $Gb_3$ in Fabry patient's fibroblasts was significantly decreased after treatment with moss-aGal or high-mann aGal for 4 days (FIG. 6b), suggesting that moss α-gal A enzymes are able to degrade the accumulated substrates in the lysosomes.

Intravenously infused enzyme in ERT is best taken up by the vascular endothelium, which forms the first barrier between blood and rest of the tissues. Furthermore, endothelial cells are a major disease-relevant cell type in some LSD such as Fabry disease. Therefore, we tested enzymatic uptake in Fabry patient-derived microvascular endothelial cells (IMFE1). IMFE1 cells were MR positive when determined by western blot and immunostaining (FIG. 6c,d). After an overnight incubation, moss α-gal A enzymes were efficiently taken up by IMFE1 cells (FIG. 6e). The uptake of moss-aGal or high-mann aGal by IMFE1 cells was predominantly blocked by yeast mannan (~60-80% inhibition) and was inhibited by M6P at a less extent (~2-10%), suggesting that MR mainly contributes to this uptake. The uptake of agalsidase alfa or agalsidase beta by IMFE1 cells was mostly inhibited by M6P (~75-82%) but also by mannan.

In vitro uptake typically reaches a plateau phase after overnight incubation. To compare uptake rates of different α-gal A preparations in a dynamic phase, IMFE1 cells were incubated with the enzymes (10 µg/ml) for shorter time. Uptake of high-mann aGal and agalsidase alfa was approximately linear for up to 3 hours, with significantly higher uptake rate of high-mann aGal than agalsidase alfa (FIG. 6f). Uptake of moss-aGal was remarkably higher than high-mann aGal and agalsidase alfa after 1-hour incubation, and reached a plateau in 1-3 hours (FIG. 6f). Similar results were obtained in repeated experiments including one with higher enzyme amount (40 µg/ml). Western blot further confirmed these results at the protein level (FIG. 6g).

To assess enzyme binding efficiencies, IMFE1 cells were incubated with different enzyme preparations (10 µg/ml) at 4° C. in the presence or absence of M6P or mannan. Three hours later, cell surface-bound α-gal A was measured by enzyme activity assay. Under this experimental condition, no α-gal A activity above background level was detected (activity of untreated cells) in cells incubated with high-mann aGal or agalsidase alfa (FIG. 6h). Moss-aGal had significantly higher cellular binding than high-mann aGal or agalsidase alfa (FIG. 6h). Binding of moss-aGal was significantly blocked by mannan but not by M6P.

These results showed that in an assay system using cultured microvascular endothelial cells, which is likely more relevant to in vivo ERT than cultured fibroblasts, binding and uptake of moss α-gal A enzymes are more efficient than agalsidase alfa, and this binding/uptake occurs through the MR. These in vitro data also suggested that moss-produced enzymes could be suitable for ERT in vivo. Since binding/uptake of moss-aGal was more efficient than high-mann aGal, we selected the former for subsequent animal studies.

Example 5.2: In Vitro Binding Study

IMFE1 cells in multi-well plate were incubated with α-gal A enzymes (10 µg/ml) at 4° C. in the presence or absence of 5 mM M6P or 2 mg/ml mannan. Culture medium EGM-2MV supplemented with 25 mM HEPES was used. Three hours later, the cells were washed with ice-cold PBS for 4 times, and were directly lysed in 0.2% Triton at 4° C. The lysates were used for protein assay and α-gal A enzyme assay.

Example 5.3: SDS-PAGE and Western Blot

Samples were denatured in LDS sample buffer (Invitrogen) with 2.5% 2-mercaptoethanol at 70° C. for 10 min. NuPAGE Bis-Tris 4-12% or 10% gels (Invitrogen) were used for protein separation. Western blot was performed as described previously (Shen et al. (2008) *Biochem Biophys Res Commun* 369:1071-1075). Primary antibodies used were rabbit polyclonal antibody to human α-gal A (Shire Human Genetic Therapies, Cambridge, Mass.), mouse monoclonal antibody to mannose receptor (clone 15-2, Abcam, Cambridge, Mass.) and goat polyclonal antibody to GAPDH (Santa Cruz Biotechnology, Santa Cruz, Calif.). The α-gal A protein levels were quantified by densitometry using ImageJ software.

Example 5.4: Immunofluorescence

Fluorescence immunostaining was performed as described previously (Shen et al. (2008) *Mol Genet Metab* 95:163-168). Primary antibodies used were mouse monoclonal antibodies to $Gb_3$ (Seikagaku, Tokyo, Japan) and mannose receptor (clone 15-2, Abcam). The cells were counterstained with DAPI.

Example 5.5: Animals and Procedures

Fabry mice were produced by breeding pairs of hemizygous males and homozygous females. Adult (3-6 months old) female Fabry mice were used throughout the study. For each experiment, animals with the same age were used. For $Gb_3$ clearance studies, female Fabry mice are more suited than male Fabry mice, because male mice have testosterone-induced $Gb_3$ synthesis in kidneys that confounds the effect of the infused enzyme in degradation of accumulated $Gb_3$. For all the injections, enzyme preparations were diluted in saline to a total volume of 200 µl per mouse and were injected into Fabry mice via tail vein.

Example 5.6: Plasma Pharmacokinetics

Enzyme preparations were injected at a dose of 1 mg/kg body weight (n=5 each). Blood samples were collected by tail bleed using heparinized capillaries at 1, 5, 10, 20 and 30 min after injection. Plasma was separated and α-gal A enzyme activity in plasma was measured.

Moss-aGal or agalsidase alfa was injected into Fabry mice via tail-vein at a dose of 1 mg/kg body weight (BW), and plasma clearance was analyzed by an in vitro α-gal A enzyme assay. Moss-aGal was more rapidly cleared from circulation than agalsidase alfa (FIG. 7*a*). To verify that the shorter plasma half-life of moss-aGal is due to more robust uptake by tissues rather than faster enzyme inactivation (denaturation) in the circulation, enzymes in mouse plasma were analyzed by western blot (FIG. 7*b*). According to the higher reactivity of the antibody to moss-aGal (FIG. 5*b*), the intensities of moss-aGal bands were corrected by a factor of 2.14. Results revealed that α-gal A protein levels in moss-aGal-infused mice at 5 and 10 min after infusion were significantly lower than in agalsidase alfa-injected mice (FIG. 7*c*). Protein levels of moss-aGal in plasma at 5 and 10 min were 37% and 28% of that of agalsidase alfa respectively, which were roughly consistent with the enzyme activity data (specific activities in moss-aGal-injected mouse plasma at these 2 time points were 49% and 28% of that in agalsidase alfa-injected mice). Furthermore, there was a strong correlation between protein levels and enzyme activities in plasma (FIG. 7*d*). Together with in vitro uptake study findings (FIG. 6*f-h*), these data suggested that intravenously administered moss-aGal is more efficiently taken up by vascular endothelial cells and other cell types in the tissues when compared to agalsidase alfa.

Example 5.7: Biodistribution

Enzyme preparations were injected at a dose of 1 mg/kg body weight (n=5 each). Two hours after injection, mice were perfused with saline (to remove blood), and heart, kidneys, spleen and liver were harvested. The whole organs were homogenized, and α-gal A activity was measured. For kidney, both kidneys were combined and homogenized.

Two hours after intravenous injection of either moss-aGal or agalsidase alfa into Fabry mice (1 mg/kg BW), tissue distribution of each enzyme preparation was assessed. Kidneys from moss-aGal-injected mice had significantly higher enzyme activities than agalsidase alfa (FIG. 8*a*). The levels of moss-aGal and agalsidase alfa in the heart and spleen were comparable (FIG. 8*a*). The level of moss-aGal in the liver was significantly lower than that of agalsidase alfa (FIG. 8*a*). Activities per whole organs were calculated and ratios between different organs were compared (FIG. 8*b*). Among total recovered activities, 94.9% of moss-aGal and 97.5% of agalsidase alfa were delivered to the livers ($P<0.05$). Kidneys of moss-aGal-injected mice had 1.96% of total activity, which is significantly higher ($P<0.05$) than that in agalsidase alfa-injected mice (0.58%). Western blot analysis confirmed the higher uptake of moss-aGal in the kidney compared to agalsidase alfa (FIG. 8*c*).

To investigate cellular distribution of the infused enzymes, immunohistochemistry was performed on Fabry mouse tissues 24 hours after injection of either moss-aGal or agalsidase alfa at 1 mg/kg BW. Specific signals displayed granular cytoplasmic pattern, presumably reflecting lysosomal localization of the enzyme. Cellular localization of these 2 enzymes in the heart and kidney was essentially identical. In hearts, both moss-aGal and agalsidase alfa were detected in capillaries and perivascular cells but not in myocytes (FIG. 9*a*). Specific staining was only seen in kidney cortical tubular epithelial cells for either enzyme (FIG. 9*b*). These results are consistent with cellular distribution of agalsidase alfa.

Example 5.8: Immunohistochemistry

Moss-aGal or agalsidase alfa was injected via tail-vein at a dose of 1 mg/kg body weight (n=2 each). Heart and kidney were harvested 1 day after enzyme infusion. Untreated female Fabry mouse tissues were used as negative controls. Tissues were fixed in formalin, embedded in paraffin, and 5-micron sections were made. Immunohistochemistry was performed by Histopathology and Tissue Shared Resource in Georgetown University (Washington, D.C.). In brief, after heat-induced epitope retrieval in citrate buffer, sections were treated with 3% hydrogen peroxide and 10% normal goat serum, and were incubated with rabbit polyclonal antibody to human α-gal A (Shire). After incubation with HRP-labeled secondary antibody, signals were detected by DAB chromogen, and the sections were counterstained with hematoxylin. Signal specificity was verified with control staining, in which the primary antibody incubation was omitted. Compared to light and diffuse non-specific staining in untreated controls, specific signal displayed granular cytoplasmic pattern.

Example 5.9: Tissue Stability

Moss-aGal or agalsidase alfa was injected via tail-vein at a dose of 1 mg/kg body weight. At 24, 48 and 96 hours post-injection, mice (n=4-5 per group) were perfused and organs were harvested and homogenized as described in Biodistribution above.

Example 5.10: Tissue Kinetics

In vivo kinetics of moss-aGal and agalsidase alfa in various organs were investigated following a single intravenous injection. At 2 and 24 hours post-injection, kidneys from moss-aGal-injected mice had significantly higher enzyme activities compared to agalsidase alfa-injected mice (FIG. 10a). However, activities were similar at 48 and 96 hours (FIG. 10a). In the heart, there was no significant difference between two forms of enzymes at 2 and 24 hours; however, activities of moss-aGal were lower than agalsidase alfa at 48 and 96 hours post-injection (FIG. 10b). In comparison to agalsidase alfa-injected mice, moss-aGal-injected mice had similar level of activities in the spleen, and significantly lower activities in the liver at all time points analyzed (FIG. 10c,d). The half-lives of moss-aGal and agalsidase alfa in the kidney and heart ranged from 2 to 3 days. Moss-aGal had a ~25% shorter half-life in both organs. The half-life of moss-aGal in the liver was significantly shorter compared to agalsidase alfa (24 vs. 57 hours). The half-lives of both enzyme forms in the spleen were similar (~30 hours).

Example 5.11: Clearance of Tissue $Gb_3$

Six months old female Fabry mice were used. Moss-aGal or agalsidase alfa was injected via tail-vein at doses of 0.3, 1 and 3 mg/kg body weight (n=4-5 each). Heart, kidney and liver were harvested 1 week after a single injection. Age- and sex-matched untreated Fabry and WT mice were used as controls (n=5). Tissues were homogenized and were subjected to glycosphin-golipids extraction and subsequent analysis of $Gb_3$ by mass-spectrometry as described previously (Durant et al. (2011) J Lipid Res 52:1742-1746). Eight isoforms were analyzed and the results shown are the sum of these isoforms. $Gb_3$ content was expressed as μg/mg total protein.

Efficacies of moss-aGal and agalsidase alfa in degrading accumulated $Gb_3$ were compared at 7 days after a single intravenous injection of either enzyme to 6 months old Fabry mice. Three different doses (0.3, 1 and 3 mg/kg BW) were tested. Untreated Fabry mice had significantly increased $Gb_3$ levels in kidney, heart and liver compared to untreated WT controls (FIG. 11a-c). Both forms of enzymes reduced $Gb_3$ in these organs in a dose-dependent manner (FIG. 11a-c). Moss-aGal and agalsidase alfa had comparable efficacy in clearing $Gb_3$ in the kidney and heart (FIG. 11a,b), except for a better cardiac $Gb_3$ clearance of agalsidase alfa at the highest dose (3 mg/kg). In clearing liver $Gb_3$, agalsidase alfa was much more effective than moss-aGal at doses of 0.3 and 1 mg/kg (FIG. 11c). At a higher dose (3 mg/kg), these 2 enzymes led to similar liver $Gb_3$ levels.

Example 6: Delivery of Moss-Produced Recombinant Human α-Galactosidase A to Mouse Model of Fabry Disease Via Non-Intravenous Routes The purpose of these experiments is to test the potential usefulness of non-intravenous routes in delivery of moss αGal to target tissues in the mouse model.

Example 6.1: Methods

Moss-aGal as described in example 1 was used in a concentration of 0.69 mg/ml. Adult (8-11 months) male Fabry mice were used. Moss aGal was injected via intraperitoneal (i.p.), intramuscular (i.m.) or subcutaneous (s.c.) routes. For the latter two routes, enzyme was injected into thigh muscles (both sides) and under the loose skin between shoulders, respectively. Doses of 1, 3 or 10 mg/kg body weight were tested. Blood was collected at 0.5, 1, 2, 4, 6 and 24 hours post-injection, and organs were dissected at 24 hours. Samples were stored at −80 C until use. Plasma from untreated Fabry mice (n=5) was used for baseline activity. α-Gal A activities in plasma and tissues were measured using standard 4MU method.

Spectrometry:

After enzyme reactions, fluorescence intensity of released 4MU was measured using SpectroMax M5 (Molecular Devices). This equipment was used for analysis of samples from i.p. and i.m. injected mice (and all the samples we have assayed in recent 5 years). However, because mechanical problem occurred recently, for s.c. injected mouse samples the fluorescence was measured using SpectroMax Paradigm (Molecular Devices). 4MU standard curve in SpectroMax Paradigm showed excellent linearity, and α-gal A activities of mouse tissues and plasma analyzed were very close to those previously measured using SpectroMax M5 (tested the same samples). Therefore, data variation by using 2 different spectrometries in this study should be very small.

Example 6.2: Results and Discussions i.p. Route (FIG. 12):

Plasma activities reached peak in 0.5-2 hours after injection, decreased thereafter and returned to baseline level at 6 hours. Activities were dose-dependent. Activities in heart, kidney, liver and spleen increased in a dose-dependent manner.

i.m. Route (FIG. 13):

Plasma activities reached peak at 0.5 hour after injection, decreased rapidly thereafter and returned to baseline level at 4 hours. Activities in heart, kidney, liver and spleen increased in a dose-dependent manner. One mouse (#14, with dose of 10 mg/kg) had markedly higher tissue activities than others in the same group; this sample was removed from data analysis.

s.c. Route (FIG. 14):

Plasma activities showed similar pattern as i.m. administration. Overall, tissue activities increased in a dose-dependent manner. However, there was no substantial difference in heart and kidney activities between doses of 1 and 3 mg/kg; this may be due to relatively limited absorption rate of this route. At the dose of 10 mg/kg, tissue activities showed large variations; 2 out of 5 mice had dramatically higher activities than the rest.

Example 6.3: Comparisons

Enzyme delivery efficiency is in the order of i.p.>s.c. (or similar) i.m.

i.p. Vs. i.v.:

α-Gal A activities in heart, kidney, liver and spleen in i.p. injected mice (1 mg/kg) were 16%, 49%, 17% and 35% those of i.v. injected mice (data from Tissue Stability study, 1 mg/kg, 24 hours post-injection).

s.c. Vs. i.p./i.v.:

Although s.c. injection led to less enzyme delivery to the tissues than i.p. injection, the ratio of decrement in different organs was not proportional. At dose of 1 mg/kg, α-gal A activities in heart, kidney, liver and spleen in s.c. injected mice were 67%, 43%, 22% and 24% those of i.p. injected mice. This suggests s.c. route tends to deliver more enzyme to heart and kidneys relative to liver and spleen. Similar pattern was seen when compared with i.v. administration. Activities in above organs of s.c. were 11%, 21%, 4% and 9% of that in i.v. injected mice.

Non-iv routes are an alternative approach for ERT. i.p. seems a good method. Considering use in human, s.c. may be a good candidate. Although tissue amounts are lower than in i.v. administration, sufficient amounts can be administered since only low amounts are needed in tissues. If low tissue activities (e.g., s.c. vs i.v.) of single administration should be insufficient to degrade accumulated $Gb_3$ in heart and kidneys, repeated injections can overcome this problem. In summary, the positive aspects of i.p., i.m. and s.c. administration like improved patient acceptance outweigh the reduced target tissue distribution.

Example 7: Discussion

Depending on the proteins characteristics as well as on its planned application, different expression hosts are chosen. Whereas bulk proteins for industrial and food-/feed applications are mostly expressed in prokaryotic hosts like *Escherichia coli*, pharmaceutical protein production often relies on expression in higher eukaryotic cells like e.g. CHO-(Chinese-hamster-ovary) or plant cells. The latter choices are mainly based on the fact pharmaceutical proteins, mostly being of human origin, require complex post-translational modifications (PTMs) such as e.g. N-glycosylations. Therefore, parallel recombinant expression of the same protein in different eukaryotic expression systems yields different product qualities with respect to PTM. For instance in case of N-glycosylation, mammalian cell expression systems tend to yield a very heterogeneous product mixture with several tens to hundreds of different N-glycan species on the same protein product. Plant-based expression systems in contrast feature a very homogenous N-glycosylation pattern with only a few (typically below ten) different glycan species present on the produced protein.

In the case of pharmaceutical protein production, the choice of the production system is often triggered by the structural and quality demands of the product. The present invention was driven by the need to produce a recombinant lysosomal protein to treat patients suffering from LSD. As these patients lack a functional version of this enzyme due to inheritable gene mutation, the recombinant product is used as a replacement by means of regular enzyme replacement therapy (e.g. intravenous infusion). For efficient uptake from the blood stream by binding to the mannose-receptor on surface of the target cells, the enzyme needs to be decorated with N-glycans bearing terminal mannose residues.

In order to produce a version of aGal with mannose-terminated N-glycans in a plant expression system, the routine method would have used vacuolar targeting of the protein by adding a secretion signal to the N-terminus and a vacuolar targeting signal to the C-terminus. In this approach, the secretion signal directs the nascent protein into the endoplasmic reticulum (ER) where it is decorated with precursor-glycans. Following the default secretory pathway, the protein is shipped to the Golgi-apparatus and its glycans will be further trimmed and processed up to a typical complex plant-N-glycan form. These glycans end with two terminal N-acetylglucosamin (GlcNAc) residues covering both possible mannose ends of such a glycan.

Exposure of these two mannoses at the second-last positions of the two glycan arms is then achieved by the second targeting peptide, the vacuolar targeting signal at the C-terminus. This peptide binds to vacuolar sorting receptors in the trans-Golgi-network (TGN) and initiates targeting of the attached protein to the vacuole. Here, beta-N-Acetyl-hexosaminidase cleaves off the terminal GlcNAcs and thereby exposes the mannose residues. The resulting glycans are classified as "paucimannosidic" and are typical for plant vacuolar proteins.

The present invention, in contrast, omits the step of incorporating a C-terminal vacuolar signal into the proteins sequence. Therefore, the recombinant product is not sorted to the vacuole in the TGN, but further follows the default secretory pathway. In this approach, trimming of the complex N-glycans and the associated exposure of terminal mannoses is not expected, as paucimannosidic structures are assigned to be vacuole-specific (Castilho & Steinkellner, 2012, *Biotechnology Journal*, 7(9), 1088-1098).

The present invention achieved N-glycan-trimming in bryophytes to generate a recombinant version of lysosomal proteins with exposed terminal mannoses on its N-glycans without a vacuolar signal. This leads to a secretory pathway that nonetheless, independent of vacuolar glycol-processing led to a product with high amounts of paucimannosidic glycoproteins in case of lysosomal proteins.

Moss-aGal was efficiently taken up by endothelial cells that express MR, and this uptake was blocked by yeast mannan, a specific inhibitor of MR-mediated endocytosis. Moss-aGal was not effectively taken up by human skin fibroblasts which do not express MR. These findings indicate that uptake of moss-aGal is mediated by MR. By contrast, uptake of agalsidase alfa involved both MR and M6PR. Animal studies revealed that enzyme activity and storage clearance capacity of moss-aGal in mouse hearts and kidneys are overall comparable to that of agalsidase alfa. These results suggest that mannose-terminated enzymes can be as effective as M6P-harboring enzymes in the treatment of Fabry disease and in other LSDs.

The tested moss-aGal is identical to its human counterpart with respect to protein sequence and -structure. Homogenous and predominantly mannose-terminated N-glycosylation is achieved by expression in a customized moss strain. Furthermore, for the production of high-mann aGal, GNT-I (N-acetyltransferase-glycosaminyltransferase I) has been knocked out. Transfer of an N-acetylglucosamine to the nascent glycan by this enzyme forms an essential substrate for their further processing to complex forms. Therefore complex glycan processing is blocked in this knockout and all glycoforms are of the high-mann type.

Our study showed that moss is a useful platform to express α-gal A and other lysosomal enzymes. In one aspect, moss per se features an outstandingly homogenous N-glycosylation, i.e. as compared to e.g. mammalian cells their proteins exhibit a drastically reduced number of glycoforms with a highly reproducible percentual distribution. With regard to pharmaceutical production this is highly advantageous in cases where N-glycan qualities are decisive for the therapeutic efficacy of a protein.

The uptake of moss-aGal by endothelial cells was much more efficient than that of agalsidase alfa. This was consistent with the faster clearance of infused moss-aGal from circulation in vivo. Given that endothelial cells may play an important role in pathophysiology of vasculopathy and other manifestations in Fabry disease, effective delivery to the endothelial cells is advantageous in preventing and correcting disease pathology. Our study also showed that, in spite of increased terminal mannose residues, binding/uptake of high-mann aGal to endothelial cells was significantly less efficient than paucimannosidic moss-aGal. This suggested that MR binding efficiency possibly depends more on the conformation of glycans, rather than absolute number of exposed mannose residues.

By immunohistochemistry, moss-aGal was detected in vascular endothelium and perivascular cells in the heart, which is overall consistent with MR distribution pattern. It is known that cardiomyocytes endocytose mannosylated ligands via MR or MR-like receptors. Although the enzyme was not detected in muscle cells, the significantly decreased cardiac $Gb_3$ (~45% decrement in Fabry mice received 1.0 or 3.0 mg/kg moss-aGal) suggests that small amount of enzyme that is under detection limit of our immunostaining method might be delivered to cardiomyocytes. In the kidney, moss-aGal was only detected in tubular epithelial cells. The mechanism for this uptake is unclear as renal tubules have not been reported to express MR. A potential interpretation is that tubular cells express other receptor(s) that mediates endocytosis of mannose-terminated glycoproteins. The presence of such unidentified receptor(s) that has MR-like binding activity has been reported in murine spleen and lymph node. Reabsorption of filtered enzymes by tubular cells through megalin-mediated endocytosis is another possibility.

Moss-aGal and agalsidase alfa displayed different tissue distributions when analyzed 2 hours after infusion. Relative to agalsidase alfa, targeting of moss-aGal to the kidney was significantly enhanced and the delivery to the liver was significantly reduced. This distribution pattern of moss-aGal is advantageous, as kidney is one of the main organs affected in this disease. In the liver, infused agalsidase alfa is delivered to both hepatocytes and sinus lining cells (endothelium and/or Kupffer cells) presumably through M6PR, asialoglycoprotein receptors and MR. Most M6PR accessible to infused phosphorylated enzyme is contained in the liver. In contrast, moss-aGal will be preferentially delivered to endothelial and Kupffer cells via MR.

The half-life of internalized moss-aGal in the heart and kidney was shorter than agalsidase alfa. This is likely related to lower carbohydrate content in moss-aGal that may lead to increased susceptibility of the enzyme to proteolytic degradation in the lysosomes. Because of the faster turnover, activity of moss-aGal in the kidney 4 days after infusion was similar to that of agalsidase alfa. The reduction of $Gb_3$ storage in the kidney and heart mirrored the residual enzyme activities at 4 days post-injection.

The comparison of moss-aGal and agalsidase alfa can serve as a useful model to study the roles of M6PR and MR in tissue uptake of agalsidase alfa. As mentioned, both M6PR and MR mediate delivery of agalsidase alfa in vitro, thus it is difficult to determine which receptor pathway is more responsible for the biodistribution and for the therapeutic response of this enzyme in a certain target organs. Despite markedly different sugar chains, cellular localization of agalsidase alfa and moss-aGal in the heart and kidney was surprisingly similar. Storage clearance efficacy in these organs was similar as well. In other words, compared to a completely non-phosphorylated enzyme, M6P residues in agalsidase alfa did not lead to a wider distribution and more complete $Gb_3$ clearance as one might expect. These findings suggested that MR pathway might play a more important role than M6PR in targeting agalsidase alfa to the heart and kidney.

The invention claimed is:

1. A lysosomal protein composition comprising a plurality of lysosomal proteins that are glycosylated according to a glycosylation pattern, wherein said glycosylation pattern has at least 60% paucimannosidic N-glycans (molar %), wherein the paucimannosidic N-glycan comprises the structure of formula 1:

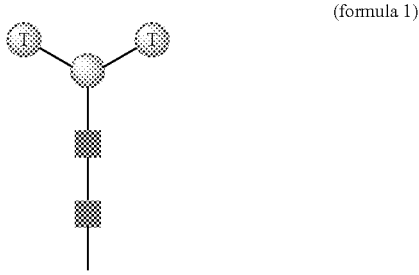

(formula 1)

wherein a square represents N-Acetylglucosamine (GlcNAc), a circle represents mannose (Man), and a circle with a T represents a terminal mannose, wherein one or more of the GlcNAc or Man subunits may be α1,3-fucosylated, α1,6-fucosylated and/or β1,2-xylosylated.

2. The lysosomal protein composition according to claim 1 wherein the lysosomal protein comprises at least one of α-Galactosidase; α-Mannosidase; Aspartylglucosaminidase; β-Mannosidase; Acid Ceremidase; α-Fucosidase; β-Galactosidase, β-Hexosaminidase activator protein; Galactocerebrosidaseb; Galactoceramidase; lysosomal acid lipase (LAL); α-Iduronidase; Iduronate-2-sulfatase; Glucosamine-N-sulfatase; Heparansulfatsulfamidase (SGSH); α-N-acetyl-glucosaminidase (NAGLU); α-glucosaminide-N-acetyltransferase; N-Acetygalactosamine-6-sulfatase; β-Galactosidase; N-Acetygalactosamine-4-sulfatase; β-Glucoronidase; Neuraminidase; Sphingomyelinase; Sphingomyelin phosphodiesterase; Acid alpha-1,4-glucosidase; β-Hexosaminidase, or its a subunit; Alpha-N-acetylgalactosaminidase (NAGA); α-Galactosaminidase; β-Hexosaminidase A; Galactose-6-sulfate sulfatase; and Hyaluronidase.

3. The lysosomal protein composition according to claim 1, wherein one or more of the GlcNAc or Man subunits may be α1,6-fucosylated.

4. The lysosomal protein composition according to claim 1 wherein the glycosylation pattern has at least 1% N-glycans of the formula GlcNAc$_2$-Hex$_2$-methyl-Hex; and/or wherein the glycosylation pattern comprises the following N-glycans:

0% to 35% -GlcNAc$_2$-(Man$_2$methyl-Hex);
30% to 80% -GlcNAc$_2$-Man$_3$;
0% to 30% -GlcNAc$_2$-Man$_3$-GlcNAc;
0% to 15% -GlcNAc$_2$-Man$_3$-GlcNAc$_2$;
0% to 5% -GlcNAc$_2$-Man$_3$-Hex$_2$,
0% to 11% -GlcNAc$_2$-Man$_3$-Hex$_3$;
0% to 10% -GlcNAc$_2$-Man$_3$-Hex$_4$;
0% to 10% -GlcNAc$_2$-Man$_3$-Hex$_5$;

wherein all of these compounds together amount to 100% or less than 100%, wherein GlcNAc is a N-Acetylglucosamine subunit, Man is a mannose subunit, Hex is a hexose subunit, methyl-Hex is a methylated hexose subunit; with the proviso that -GlcNAc$_2$-(Man$_2$methyl-Hex) and -GlcNAc$_2$-Man$_3$ together amount to at least 45%, (all % are molar %); wherein the GlcNAc at the reducing end of the glycan is not fucosylated in any one of the above N-glycans; wherein a Man at a branching point, is not xylosylated in any one of the above N-glycans.

5. The lysosomal protein composition according to claim 1 comprising non-phosphorylated lysosomal proteins.

6. An in vitro method of processing a lysosomal protein comprising a complex N-glycan, said method comprising providing the lysosomal protein of claim 1 in a sample and contacting the sample with a bryophyte HEXO, whereby the bryophyte HEXO enzyme cleaves terminal GlcNAc residues from the lysosomal protein thereby producing a paucimannosidic N-glycan.

7. The method of treatment of a lysosomal storage disease comprising administering a lysosomal protein composition according to claim 1.

8. The lysosomal protein composition according to claim 2, wherein the α-Galactosidase is selected from α-Galactosidase A (GLA); ß-Glucoceramidase, and β-glucosidase (glucocerebrosidase).

9. The lysosomal protein composition according to claim 4, wherein the glycosylation pattern further comprises at least one of the following N-glycans:

1% to 30% -GlcNAc$_2$-(Man$_2$methyl-Hex);
40% to 70% -GlcNAc$_2$-Man$_3$;
4% to 22%, -GlcNAc$_2$-Man$_3$-GlcNAc;
2% to 12% -GlcNAc$_2$-Man$_3$-GlcNAc$_2$;
0% to 3% -GlcNAc$_2$-Man$_3$-Hex$_2$,
1% to 8% -GlcNAc$_2$-Man$_3$-Hex$_3$;
1% to 7% -GlcNAc$_2$-Man$_3$-Hex$_4$;
1% to 7% -GlcNAc$_2$-Man$_3$-Hex$_5$.

10. The lysosomal protein composition according to claim 4, wherein methyl-Hex is 2-0 methyl hexose.

11. The lysosomal protein composition according to claim 4, wherein Hex is Man.

12. The lysosomal protein composition according to claim 1, wherein the glycosylation pattern has at least 45% paucimannosidic N-glycans (molar %) that are not α1,3-fucosylated and that are not β1,2-xylosylated.

13. The in vitro method of processing a lysosomal protein comprising a complex N-glycan according to claim 6, wherein said bryophyte HEXO is an HEXO3 enzyme.

14. The method of treatment of a lysosomal storage disease according to claim 7 wherein the disease and lysosomal protein are selected from the following table:

| Disease | lysosomal protein |
| --- | --- |
| Fabry Disease | α-Galactosidase A (GLA) |
| Gaucher's Disease | β-Glucoceramidase, β-glucosidase (glucocerebrosidase) |
| Alpha-Mannosidosis | α-Mannosidase |
| Aspartylglucosaminuria | Aspartylglucosaminidase |
| Beta-Mannosidosis | β-Mannosidase |
| Farber Disease | Acid Ceremidase |
| Fucosidosis | α-Fucosidase |
| GM1-Gangliosidosis | β-Galactosidase, β-Hexosaminidase activator protein |
| Krabbe Disease | Galactocerebrosidase; Galactoceramidase |
| Lysosomal Acid Lipase (LAL) Deficiency | lysosomal acid lipase (LAL) |
| Mucopolysaccharidoses | α-Iduronidase |
| | Iduronate-2-sulfatase |
| | Glucosamine-N-sulfatase; Heparansulfatsulfamidase (SGSH) |
| | α-N-acetyl-glucosaminidase (NAGLU) |
| | α-glucosaminide-N-acetyltransferase |
| | N-Acetygalactosamine-6-sulfatase |
| | Galactose-6-sulfate sulfatase |
| | β-Galactosidase |
| | N-Acetygalactosamine-4-sulfatase |
| | β-Glucoronidase |
| | Hyaluronidase |
| Niemann Pick Disease | Sphingomyelinase |
| Pompe Disease | (Acid) alpha-1,4-glucosidase |
| Sandhoff Disease | β-Hexosaminidase, or its α subunit |
| Schindler Disease | Alpha-N-acetylgalactosaminidase (NAGA); α-Galactosaminidase |
| Tay-Sachs Syndrome | β-Hexosaminidase A |
| Sialidosis | Neuraminidase. |

15. The lysosomal protein composition according to claim 1, wherein one or more of the mannose is methylated.

\* \* \* \* \*

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: vacuolar signal

<400> SEQUENCE: 1

Val Asp Thr Met
1

<210> SEQ ID NO 2
<211> LENGTH: 4
<212> TYPE: PRT
<213> ORGANISM: Artificial Sequence
<220> FEATURE:
<223> OTHER INFORMATION: ER retention signal peptide

<400> SEQUENCE: 2

Lys Asp Glu Leu
1

<210> SEQ ID NO 3
<211> LENGTH: 398
<212> TYPE: PRT
<213> ORGANISM: Homo sapiens

<400> SEQUENCE: 3

Leu Asp Asn Gly Leu Ala Arg Thr Pro Thr Met Gly Trp Leu His Trp
1               5                   10                  15
```

Glu Arg Phe Met Cys Asn Leu Asp Cys Gln Glu Pro Asp Ser Cys
                20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu
385                 390                 395

<210> SEQ ID NO 4
<211> LENGTH: 1197
<212> TYPE: DNA
<213> ORGANISM: Homo sapiens

<400> SEQUENCE: 4

```
ttggataatg gattggctag aactcctact atgggatggt tgcattggga gagattcatg      60
tgcaacttgg actgccaaga ggaacctgat tcttgcatct ctgagaagct gttcatggaa     120
atggctgagt tgatggtgtc tgagggatgg aaggatgctg atacgagta cttgtgcatt      180
gatgattgct ggatggctcc tcagagagat tctgagggaa gattgcaggc tgatcctcag     240
agattccctc atggaattag gcagttggct aactacgtgc actctaaggg attgaagttg     300
ggcatctacg ctgatgtggg aaacaagact tgcgctggat tccctggatc tttcggctac    360
tacgatattg acgctcagac tttcgctgat tggggagtgg atttgttgaa gttcgatgga    420
tgctactgcg acagcttgga gaatttggct gatggataca agcacatgag cttggctttg    480
aataggactg gacggtctat tgtgtactct tgcgagtggc ctctgtacat gtggccttc     540
cagaagccta actacactga gattaggcag tactgcaacc actggcgaaa cttcgctgat    600
atcgatgact cttggaagtc catcaagtct atcctggatt ggaccagctt caatcaagag    660
cgaattgtgg atgtggctgg acctggtgga tggaatgatc ctgatatgtt ggtgatcgga    720
aacttcggac tgtcttggaa tcagcaagtg actcagatgg ctctgtgggc tattatggct    780
gctccttgt tcatgagcaa cgatttgagg catattagcc ctcaggctaa ggctttgttg     840
caggataagg atgtgatcgc tatcaaccag gatccttggg gaaagcaggg ataccagttg    900
agacagggtg ataatttcga ggtgtgggag aggccttgt ctggattggc ttgggctgtg     960
gctatgatta acagacaaga gattggaggc cctcggagct atacaattgc tgtggcttct   1020
ttgggaaagg gtgtggcttg caatcctgct tgcttcatta ctcagttgtt gcccgtgaag   1080
aggaagttgg gattctacga gtggacttct aggttgcggt cacacattaa ccctactgga   1140
actgtgttgc tgcagttgga gaacactatg cagatgagct gaaggatct gctgtga       1197
```

<210> SEQ ID NO 5
<211> LENGTH: 26
<212> TYPE: PRT
<213> ORGANISM: Physcomitrella patens

<400> SEQUENCE: 5

```
Met Ala Phe Tyr Lys Ile Ser Ser Val Phe Ile Phe Cys Phe Phe
1               5                   10                  15
Leu Ile Ala Leu Pro Phe His Ser Tyr Ala
            20                  25
```

<210> SEQ ID NO 6
<211> LENGTH: 497
<212> TYPE: PRT
<213> ORGANISM: Homo sapiens

<400> SEQUENCE: 6

```
Ala Arg Pro Cys Ile Pro Lys Ser Phe Gly Tyr Ser Ser Val Val Cys
1               5                   10                  15
Val Cys Asn Ala Thr Tyr Cys Asp Ser Phe Asp Pro Pro Thr Phe Pro
            20                  25                  30
Ala Leu Gly Thr Phe Ser Arg Tyr Glu Ser Thr Arg Ser Gly Arg Arg
        35                  40                  45
Met Glu Leu Ser Met Gly Pro Ile Gln Ala Asn His Thr Gly Thr Gly
    50                  55                  60
Leu Leu Leu Thr Leu Gln Pro Glu Gln Lys Phe Gln Lys Val Lys Gly
65                  70                  75                  80
```

```
Phe Gly Gly Ala Met Thr Asp Ala Ala Ala Leu Asn Ile Leu Ala Leu
                 85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
            130                 135             140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
            210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln
```

<210> SEQ ID NO 7
<211> LENGTH: 1494
<212> TYPE: DNA
<213> ORGANISM: Homo sapiens

<400> SEQUENCE: 7

```
gcccgcccct gcatccctaa gagcttcggc tacagctcgg tggtgtgtgt ctgcaatgcc      60
acatactgtg actcctttga cccccccgacc tttcctgccc ttggtacctt cagccgctat    120
gagagtacac gcagtgggcg acggatggag ctgagtatgg ggcccatcca ggctaatcac    180
acgggcacag gcctgctact gaccctgcag ccagaacaga agttccagaa agtgaaggga    240
tttggagggg ccatgacaga tgctgctgct ctcaacatcc ttgccctgtc accccctgcc    300
caaaatttgc tacttaaatc gtacttctct gaagaaggaa tcggatataa catcatccgg    360
gtacccatgg ccagctgtga cttctccatc cgcacctaca cctatgcaga caccccctgat    420
gatttccagt tgcacaactt cagcctccca gaggaagata ccaagctcaa gatacccctg    480
attcaccgag ccctgcagtt ggcccagcgt cccgtttcac tccttgccag ccctggaca    540
tcacccactt ggctcaagac caatggagcg gtgaatggga aggggtcact caagggacag    600
cccggagaca tctaccacca gacctgggcc agatactttg tgaagttcct ggatgcctat    660
gctgagcaca gttacagttt ctgggcagtg acagctgaaa atgagccttc tgctgggctg    720
ttgagtggat accccttcca gtgcctgggc ttcacccctg aacatcagcg agacttcatt    780
gcccgtgacc taggtcctac cctcgccaac agtactcacc acaatgtccg cctactcatg    840
ctggatgacc aacgcttgct gctgccccac tgggcaaagg tggtactgac agacccagaa    900
gcagctaaat atgttcatgg cattgctgta cattggtacc tggactttct ggctccagcc    960
aaagccaccc taggggagac acaccgcctg ttccccaaca ccatgctctt tgcctcagag   1020
gcctgtgtgg gctccaagtt ctgggagcag agtgtgcggc taggctcctg ggatcgaggg   1080
atgcagtaca gccacagcat catcacgaac ctcctgtacc atgtggtcgg ctggaccgac   1140
tggaaccttg ccctgaaccc cgaaggagga cccaattggg tgcgtaactt tgtcgacagt   1200
cccatcattg tagacatcac caaggacacg ttttacaaac agcccatgtt ctaccacctt   1260
ggccacttca gcaagttcat tcctgagggc tcccagagag tggggctggt tgccagtcag   1320
aagaacgacc tggacgcagt ggcactgatg catcccgatg ctctgctgt tgtggtcgtg   1380
ctaaaccgct cctctaagga tgtgcctctt accatcaagg atcctgctgt gggcttcctg   1440
gagacaatct cacctggcta ctccattcac acctacctgt ggcgtcgcca gtga         1494
```

<210> SEQ ID NO 8
<211> LENGTH: 896
<212> TYPE: PRT
<213> ORGANISM: Homo sapiens

<400> SEQUENCE: 8

```
Gln Gln Gly Ala Ser Arg Pro Gly Pro Arg Asp Ala Gln Ala His Pro
1               5                  10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60
```

-continued

```
Gln Met Gly Gln Pro Trp Cys Phe Phe Pro Ser Tyr Pro Ser Tyr
 65                  70                  75                  80

Lys Leu Glu Asn Leu Ser Ser Ser Glu Met Gly Tyr Thr Ala Thr Leu
                 85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro His Val
130                 135                 140

His Ser Arg Ala Pro Ser Pro Leu Tyr Ser Val Glu Phe Ser Glu Glu
145                 150                 155                 160

Pro Phe Gly Val Ile Val Arg Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
                245                 250                 255

Leu Asn Ser Asn Ala Met Asp Val Val Leu Gln Pro Ser Pro Ala Leu
            260                 265                 270

Ser Trp Arg Ser Thr Gly Gly Ile Leu Asp Val Tyr Ile Phe Leu Gly
        275                 280                 285

Pro Glu Pro Lys Ser Val Val Gln Gln Tyr Leu Asp Val Val Gly Tyr
290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
            340                 345                 350

Asp Ser Arg Arg Asp Phe Thr Phe Asn Lys Asp Gly Phe Arg Asp Phe
        355                 360                 365

Pro Ala Met Val Gln Glu Leu His Gln Gly Gly Arg Arg Tyr Met Met
370                 375                 380

Ile Val Asp Pro Ala Ile Ser Ser Ser Gly Pro Ala Gly Ser Tyr Arg
385                 390                 395                 400

Pro Tyr Asp Glu Gly Leu Arg Arg Gly Val Phe Ile Thr Asn Glu Thr
                405                 410                 415

Gly Gln Pro Leu Ile Gly Lys Val Trp Pro Gly Ser Thr Ala Phe Pro
            420                 425                 430

Asp Phe Thr Asn Pro Thr Ala Leu Ala Trp Trp Glu Asp Met Val Ala
        435                 440                 445

Glu Phe His Asp Gln Val Pro Phe Asp Gly Met Trp Ile Asp Met Asn
450                 455                 460

Glu Pro Ser Asn Phe Ile Arg Gly Ser Glu Asp Gly Cys Pro Asn Asn
465                 470                 475                 480

Glu Leu Glu Asn Pro Pro Tyr Val Pro Gly Val Val Gly Gly Thr Leu
```

-continued

```
                485                 490                 495
Gln Ala Ala Thr Ile Cys Ala Ser Ser His Gln Phe Leu Ser Thr His
                500                 505                 510
Tyr Asn Leu His Asn Leu Tyr Gly Leu Thr Glu Ala Ile Ala Ser His
                515                 520                 525
Arg Ala Leu Val Lys Ala Arg Gly Thr Arg Pro Phe Val Ile Ser Arg
                530                 535                 540
Ser Thr Phe Ala Gly His Gly Arg Tyr Ala Gly His Trp Thr Gly Asp
545                 550                 555                 560
Val Trp Ser Ser Trp Glu Gln Leu Ala Ser Val Pro Glu Ile Leu
                565                 570                 575
Gln Phe Asn Leu Leu Gly Val Pro Leu Val Gly Ala Asp Val Cys Gly
                580                 585                 590
Phe Leu Gly Asn Thr Ser Glu Glu Leu Cys Val Arg Trp Thr Gln Leu
                595                 600                 605
Gly Ala Phe Tyr Pro Phe Met Arg Asn His Asn Ser Leu Leu Ser Leu
                610                 615                 620
Pro Gln Glu Pro Tyr Ser Phe Ser Glu Pro Ala Gln Gln Ala Met Arg
625                 630                 635                 640
Lys Ala Leu Thr Leu Arg Tyr Ala Leu Leu Pro His Leu Tyr Thr Leu
                645                 650                 655
Phe His Gln Ala His Val Ala Gly Glu Thr Val Ala Arg Pro Leu Phe
                660                 665                 670
Leu Glu Phe Pro Lys Asp Ser Ser Thr Trp Thr Val Asp His Gln Leu
                675                 680                 685
Leu Trp Gly Glu Ala Leu Leu Ile Thr Pro Val Leu Gln Ala Gly Lys
                690                 695                 700
Ala Glu Val Thr Gly Tyr Phe Pro Leu Gly Thr Trp Tyr Asp Leu Gln
705                 710                 715                 720
Thr Val Pro Val Glu Ala Leu Gly Ser Leu Pro Pro Pro Ala Ala
                725                 730                 735
Pro Arg Glu Pro Ala Ile His Ser Glu Gly Gln Trp Val Thr Leu Pro
                740                 745                 750
Ala Pro Leu Asp Thr Ile Asn Val His Leu Arg Ala Gly Tyr Ile Ile
                755                 760                 765
Pro Leu Gln Gly Pro Gly Leu Thr Thr Thr Glu Ser Arg Gln Gln Pro
                770                 775                 780
Met Ala Leu Ala Val Ala Leu Thr Lys Gly Gly Glu Ala Arg Gly Glu
785                 790                 795                 800
Leu Phe Trp Asp Asp Gly Glu Ser Leu Glu Val Leu Glu Arg Gly Ala
                805                 810                 815
Tyr Thr Gln Val Ile Phe Leu Ala Arg Asn Asn Thr Ile Val Asn Glu
                820                 825                 830
Leu Val Arg Val Thr Ser Glu Gly Ala Gly Leu Gln Leu Gln Lys Val
                835                 840                 845
Thr Val Leu Gly Val Ala Thr Ala Pro Gln Gln Val Leu Ser Asn Gly
                850                 855                 860
Val Pro Val Ser Asn Phe Thr Tyr Ser Pro Asp Thr Lys Val Leu Asp
865                 870                 875                 880
Ile Cys Val Ser Leu Leu Met Gly Glu Gln Phe Leu Val Ser Trp Cys
                885                 890                 895
```

<210> SEQ ID NO 9

```
<211> LENGTH: 2691
<212> TYPE: DNA
<213> ORGANISM: Homo sapiens

<400> SEQUENCE: 9
```

| | | | | | |
|---|---|---|---|---|---|
| cagcagggag | ccagcagacc | agggccccgg | gatgcccagg | cacaccccgg | ccgtcccaga |   60 |
| gcagtgccca | cacagtgcga | cgtccccccc | aacagccgct | tcgattgcgc | ccctgacaag |  120 |
| gccatcaccc | aggaacagtg | cgaggcccgc | ggctgttgct | acatccctgc | aaagcagggg |  180 |
| ctgcagggag | cccagatggg | gcagccctgg | tgcttcttcc | cacccagcta | ccccagctac |  240 |
| aagctggaga | acctgagctc | ctctgaaatg | ggctacacgg | ccaccctgac | ccgtaccacc |  300 |
| cccaccttct | tccccaagga | catcctgacc | ctgcggctgg | acgtgatgat | ggagactgag |  360 |
| aaccgcctcc | acttcacgat | caaagatcca | gctaacaggc | gctacgaggt | gcccttggag |  420 |
| accccgcatg | tccacagccg | ggcaccgtcc | ccactctaca | gcgtggagtt | ctccgaggag |  480 |
| cccttcgggg | tgatcgtgcg | ccggcagctg | gacggccgcg | tgctgctgaa | cacgacggtg |  540 |
| gcgcccctgt | tctttgcgga | ccagttcctt | cagctgtcca | cctcgctgcc | ctcgcagtat |  600 |
| atcacaggcc | tcgccgagca | cctcagtccc | ctgatgctca | gcaccagctg | gaccaggatc |  660 |
| accctgtgga | accgggacct | tgcgcccacg | cccgtgcgca | acctctacgg | gtctcaccct |  720 |
| ttctacctgg | cgctggagga | cggcgggtcg | gcacacgggg | tgttcctgct | aaacagcaat |  780 |
| gccatggatg | tggtcctgca | gccgagccct | gcccttagct | ggaggtcgac | aggtgggatc |  840 |
| ctggatgtct | acatcttcct | gggcccagag | cccaagagcg | tggtgcagca | gtacctggac |  900 |
| gttgtgggat | acccgttcat | gccgccatac | tggggcctgg | gcttccacct | gtgccgctgg |  960 |
| ggctactcct | ccaccgctat | cacccgccag | gtggtggaga | acatgaccag | ggcccacttc | 1020 |
| cccctggacg | tccagtggaa | cgacctggac | tacatggact | cccggaggga | cttcacgttc | 1080 |
| aacaaggatg | gcttccggga | cttcccggcc | atggtgcagg | agctgcacca | gggcggccgg | 1140 |
| cgctacatga | tgatcgtgga | tcctgccatc | agcagctcgg | gccctgccgg | gagctacagg | 1200 |
| ccctacgacg | agggtctgcg | gagggggtt | ttcatcacca | acgagaccgg | ccagccgctg | 1260 |
| attgggaagg | tatggcccgg | gtccactgcc | ttcccccgact | tcaccaaccc | cacagccctg | 1320 |
| gcctggtggg | aggacatggt | ggctgagttc | catgaccagg | tgcccttcga | cggcatgtgg | 1380 |
| attgacatga | acgagccttc | caacttcatc | aggggctctg | aggacggctg | ccccaacaat | 1440 |
| gagctggaga | acccacccta | cgtgcctggg | gtggttgggg | ggaccctcca | ggcggccacc | 1500 |
| atctgtgcct | ccagccacca | gtttctctcc | acacactaca | acctgcacaa | cctctacggc | 1560 |
| ctgaccgaag | ccatcgcctc | ccacagggcg | ctggtgaagg | ctcgggggac | acgcccattt | 1620 |
| gtgatctccc | gctcgacctt | tgctggccac | ggccgatacg | ccggccactg | gacggggggac | 1680 |
| gtgtggagct | cctgggagca | gctcgcctcc | tccgtgccag | aaatcctgca | gtttaacctg | 1740 |
| ctggggggtgc | ctctggtcgg | ggccgacgtc | tgccggcttcc | tgggcaacac | ctcagaggag | 1800 |
| ctgtgtgtgc | gctggaccca | gctgggggcc | ttctaccccct | tcatgcggaa | ccacaacagc | 1860 |
| ctgctcagtc | tgccccagga | gccgtacagc | ttcagcgagc | cggcccagca | ggccatgagg | 1920 |
| aaggccctca | ccctgcgcta | cgcactcctc | ccccacctct | acacactgtt | ccaccaggcc | 1980 |
| cacgtcgcgg | gggagaccgt | ggcccggccc | ctcttcctgg | agttccccaa | ggactctagc | 2040 |
| acctggactg | tggaccacca | gctcctgtgg | ggggaggccc | tgctcatcac | ccagtgctc | 2100 |
| caggccggga | aggccgaagt | gactggctac | ttccccttgg | gcatggtta | cgacctgcag | 2160 |
| acggtgccag | tagaggccct | tggcagcctc | ccaccccac | ctgcagctcc | ccgtgagcca | 2220 |

```
gccatccaca gcgaggggca gtgggtgacg ctgccggccc ccctggacac catcaacgtc    2280
cacctccggg ctgggtacat catccccctg cagggccctg gcctcacaac cacagagtcc    2340
cgccagcagc ccatggccct ggctgtggcc ctgaccaagg gtggggaggc ccgagggag    2400 ctgttctggg acgatggaga gagcctggaa gtgctggagc gaggggccta cacacaggtc    2460
atcttcctgg ccaggaataa cacaatcgtg aatgagctgg tacgtgtgac cagtgaggga    2520
gctggcctgc agctgcagaa ggtgactgtc ctgggcgtgg ccacggcgcc ccagcaggtc    2580
ctctccaacg gtgtccctgt ctccaacttc acctacagcc ccgacaccaa ggtcctggac    2640
atctgtgtct cgctgttgat gggagagcag tttctcgtca gctggtgtta g            2691
```